US012714707B2

(12) United States Patent
Wu et al.

(10) Patent No.: US 12,714,707 B2
(45) Date of Patent: Aug. 25, 2026

(54) COMBINATION CANCER THERAPY USING CHK INHIBITOR

(71) Applicant: SHANGHAI HUAYU BIOTECHNOLOGY CO., LTD., Shanghai (CN)

(72) Inventors: Fan Wu, Brookline, MA (US); Zhanggui Wu, Brookline, WA (US)

(73) Assignee: SHANGHAI HUAYU BIOTECHNOLOGY CO. LTD, Shanghai (CN)

( * ) Notice: Subject to any disclaimer, the term of this patent is extended or adjusted under 35 U.S.C. 154(b) by 873 days.

(21) Appl. No.: 17/786,073

(22) PCT Filed: Jan. 6, 2021

(86) PCT No.: PCT/US2021/012295
§ 371 (c)(1),
(2) Date: Jun. 16, 2022

(87) PCT Pub. No.: WO2021/141980
PCT Pub. Date: Jul. 15, 2021

(65) Prior Publication Data

US 2023/0049029 A1 Feb. 16, 2023

Related U.S. Application Data

(60) Provisional application No. 62/957,806, filed on Jan. 7, 2020.

(51) Int. Cl.

| | |
|---|---|
| ***A61K 31/5025*** | (2006.01) |
| ***A61K 31/17*** | (2006.01) |
| ***A61K 31/405*** | (2006.01) |
| ***A61K 31/4196*** | (2006.01) |
| ***A61K 31/519*** | (2006.01) |
| ***A61K 39/00*** | (2006.01) |
| ***A61K 45/06*** | (2006.01) |
| ***A61P 35/02*** | (2006.01) |

(52) U.S. Cl.
CPC .......... *A61K 31/5025* (2013.01); *A61K 31/17* (2013.01); *A61K 31/405* (2013.01); *A61K 31/4196* (2013.01); *A61K 31/519* (2013.01); *A61K 45/06* (2013.01); *A61P 35/02* (2018.01); *A61K 2039/505* (2013.01)

(58) Field of Classification Search
CPC .......... A61K 2039/505; A61K 2300/00; A61K 31/17; A61K 31/405; A61K 31/4196; A61K 31/4745; A61K 31/495; A61K 31/501; A61K 31/5025; A61K 31/519; A61K 31/7068; A61K 33/243; A61K 45/06; A61P 35/00; A61P 35/02
See application file for complete search history.

(56) References Cited

U.S. PATENT DOCUMENTS

| | | | | |
|---|---|---|---|---|
| 8,962,626 | B2 * | 2/2015 | Wu | A61P 29/00 544/235 |
| 2010/0113452 | A1 | 5/2010 | Klien et al. | |
| 2012/0232082 | A1 | 9/2012 | Wu et al. | |

FOREIGN PATENT DOCUMENTS

| | | | |
|---|---|---|---|
| WO | WO-2004080976 A1 * | 9/2004 | A61K 31/00 |
| WO | WO-2011035077 A1 * | 3/2011 | A61P 13/12 |

OTHER PUBLICATIONS

Cecil Textbook of Medicine, 20th Ed., vol. 1 (Year: 1997).*
Wu et al., Small-molecule inhibitors, immune checkpoint inhibitors, and more: FDA-approved novel therapeutic drugs for solid tumors from 1991 to 2021; Journal of Hematology & Oncology, 15, 143 (Year: 2022).*
CAS Registry File (76311-22-0, entered into STN Oct. 15, 2004, Obtained from the internet Apr. 24, 2025) (Year: 2004).*
O'Shaugnessy, "Pemetrexed: An Active New Agent for Breast Cancer", Seminars in Oncology, 29, 6, 57-62 (Year: 2002).*
Kalindi Parmar, et al., The CHK1 Inhibitor Prexasertib Exhibits Monotherapy Activity in High-Grade Serous Ovarian Cancer Models and Sensitizes to PARP, Cancer Research (2019) vol. 25(20), pp. 6127-6140.
ISR and Written Opinion issued May 3, 2021, in International Application No. PCT/US2021/012295.

* cited by examiner

*Primary Examiner* — Jeffrey H Murray
*Assistant Examiner* — Daniel John Burkett
(74) *Attorney, Agent, or Firm* — Duane Morris LLP; Thomas J. Kowalski

(57) ABSTRACT

Disclosed are methods for treating a cancer selected from breast cancer, colon cancer, ovarian cancer, or pancreatic cancer in a subject in need thereof, comprising administering a therapeutically effective amount of a compound of formula I or a pharmaceutically acceptable salt thereof, in combination with a poly (ADP)-ribose polymerase (PARP) inhibitor. The compound of formula I acts as a checkpoint kinase (CHK) inhibitor. The combination exhibits synergistic anti-tumor efficacy, including enhanced tumor cell growth inhibition at reduced effective concentrations. Also disclosed are pharmaceutically acceptable compositions comprising the compound of formula I and a PARP inhibitor.

16 Claims, 3 Drawing Sheets

BT474

COMBINATION CANCER THERAPY USING CHK INHIBITOR

RELATED APPLICATIONS AND INCORPORATION BY REFERENCE

This application claims priority to U.S. provisional application No. 62/957,806 filed on Jan. 7, 2020.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

TECHNICAL FIELD

The present disclosure relates to the use of a checkpoint kinase (CHK) inhibitor in combination with a poly(ADP)-ribose polymerase (PARP) inhibitor, and optionally an additional chemotherapeutic agent in cancer treatment.

BACKGROUND OF THE INVENTION

Cancer is the second leading cause of deaths globally, and the average 5-year survival rates for adult patients are quite low, about 14-56% in North American.

The current options for cancer treatment traditionally included surgery, radiation therapy, chemotherapy, hormone therapy, and immunotherapy. Radiation therapy and chemotherapy remain first-line treatments for various types of cancers due to efficient destruction of cancer cells. However, these two commonly adopted therapies are toxic to patients as they usually non-selectively destroy healthy cells and cause depression of the immune system. Cancer immunotherapy involves activation of the immune system and amplification of immune responses, and was voted "breakthrough of the year" by Science in 2013. It offers an option of lesser high-grade toxicity compared with other stand therapies, and has enjoyed an unparalleled success over its peers. However, a significant subset of patients do not respond to immunotherapy as a monotherapy, probably because cancer cells develop several mechanisms to evade immune surveillance and induce immune tolerance. Targeted therapy is a medical treatment that partly overlaps the chemotherapy and immunotherapy where chemotherapeutic agents or biopharmaceuticals interfere with specific targeted molecules needed for carcinogenesis and tumor growth or tissue environment contributing to cancer growth and survival, and is sometimes less harmful to healthy cells than the traditional cytotoxic chemotherapy.

Combination therapy has emerged as a promising new cancer treatment strategy, as the combination of two or more therapeutic treatments may target more than one cancer-inducing or sustaining pathways so as to increase the chance of killing cancer cells, to minimize drug resistance, and to lower single drug dose.

Checkpoint Kinase

In eukaryotic cells, the cell cycle is regulated by checkpoints that control the transition from one phase to another. The transition through the S and G2/M phase is regulated by checkpoint kinase 1 (CHK1) and, at a lower rate, by checkpoint kinase 2 (CHK2).

The checkpoint kinases are the regulator of DNA replication and DNA damage response (DDR). In particular, studies have shown CHK1 is the master regulator of replication stress (RS) which is characterized by slowing or stalling of the replication fork and mainly caused by DNA damage, replication-transcription collision, and depletion of deoxyribonucleoside triphosphate (dNTP) pools. RS may lead to genome instability and is therefore linked with cancer cells. CHK1, in response to the RS, temporarily arrests the cell cycle and manages replication origin firing, preventing excessive DNA damage and increasing the overall survival fitness of the tumor cells (Kotsantis P, Petermann E, Boulton S J. Mechanisms of oncogene-induced replication stress: jigsaw falling into place. Cancer Discov. 2018. 8:537-555).

High expression of CHK1, along with other DDR proteins, is observed in certain cancers such as SCLC (Byers L A et al. Proteomic profiling identifies dysregulated pathways in small cell lung cancer and novel therapeutic targets including PARP1. Cancer Discov. 2012. 2:798-811; Sen T et al. CHK1 inhibition in small cell lung cancer produces single-agent activity in biomarker-defined disease subsets and combination activity with cisplatin or olaparib. Cancer Res. 2017. 77:3870-3884), and inhibition of CHK1 expression may increase the sensitivity of cancer cells to DNA damage therapy, reversing drug resistance or tolerance of cancer cells.

Combination Therapy Using CHK Inhibitor

Despite of its promising anti-tumor effects, the CHK1 inhibitor may adversely affect DNA damage repair in healthy cells and may suppress the immune system to some extent. One possible way to reduce the harm to human body while keeping the anti-tumor effect is to find a combination regimen where the CHK inhibitor works with another agent synergistically to provide a better anti-tumor therapy using a lower dose of the CHK inhibitor.

The candidate agent to be administered with the CHK inhibitor may be an inhibitor of poly(ADP)-ribose polymerase (PARP), such as Olaparib, Rucaparib, Niraparib, and Talazoparib. PARP is a family of proteins involved in DNA repair, and its main role is to detect and initiate an immediate cellular response to single-strand DNA breaks (SSB). PARP inhibitors may impair SSB repair, leading to double-strand DNA breaks (DSB). When such DSBs cannot be efficiently repaired by homologous recombination repair (HRR), e.g., in BRCA-mutant cancer cells, cancer cell death may occur (Martin S A, et al., (2008) *Curr Opin Genet Dev* 18:80-86). Researches have further found that ATR/CHK1 pathway prevents DNA DSB, and inhibition of this pathway might increase reliance on HRR. Such finding may serve as the basis for the combined use of a CHK1 inhibitor and a PARP inhibitor in treatment of cancers, especially BRCA-mutant cancers.

The CHK inhibitor may be also used in combination with a chemotherapeutic agent such as gemcitabine. Low-dose gemcitabine (LDG) is currently tested in clinical trials with several small molecule inhibitors of CHK1. The need to better understand the extent to which chemotherapy may enhance immune-checkpoint blockade (ICB) response has thus been recognized by researchers.

Gemcitabine is known to cause dNTP depletion and fork stalling, even at sub-therapeutic concentrations. The combination of LDG with CHK1 inhibitors represents a unique approach to combining chemotherapy with targeted agents. Instead of using standard-dose chemotherapy to induce cancer cell death, the LDG is used for its RS-inducing properties to increase reliance of cancer cells on CHK1 and therefore potentiate the CHK1 inhibitor's intrinsic cytotoxicity and immunostimulatory activities.

Although encouraging data have been obtained in several combination therapies, it should be noted that not all therapies or specific agents can be combined and even fewer combination treatments work in a synergistic manner. One therapeutic agent may change a secondary agent's pharmacology and thus disable its anti-tumor activity. For example, one therapeutic agent may change the conformation, or inhibit the metabolism of a secondary agent in human body, leading to the buildup of toxicity. For example, in a pooled analysis of 14 phase I-III studies, while 64% of patients receiving various doses of ipilimumab (anti-CTLA-4) experienced immune-related adverse effects, patients receiving dual therapy with anti-PD-1 mAb plus ipilimumab had a 93% incidence of adverse events (Wolchok, J. D., et al., Nivolumab plus ipilimumab in advanced melanoma. N. Engl. J. Med., 2013. 369: 122-33). Full investigation is thus needed on the interaction between two or more anti-tumor agents in a combination regimen before coming to a conclusion that whether the combination regimen is proper or not, or whether a maximum efficacy may be achieved with minimal toxicity.

SUMMARY OF THE INVENTION

The present inventor has surprisingly found that the compounds disclosed in WO2009/092278 and WO2011/035077 as the CHK inhibitors may work synergistically with a poly(ADP)-ribose polymerase (PARP) inhibitor to provide an enhanced anti-tumor effect with not elevated toxicity, suggesting this CHK inhibitor may be used in combination with a PARP inhibitor in cancer treatments.

The present inventor further surprisingly found that such a checkpoint kinase inhibitor may work synergistically with a PARP inhibitor and a chemotherapeutic agent, such as gemcitabine, to provide a further enhanced anti-tumor effect without elevated toxicity, suggesting this inhibitor may be used in combination with a PARP inhibitor and a chemotherapeutic agent in cancer treatment.

Therefore, in a first aspect, the present disclosure discloses a method for treating a cancer, comprising administering a subject in need thereof a therapeutically effective amount of a compound of formula I, or the pharmaceutically acceptable salt thereof, in combination with an immunotherapeutic agent or a therapeutic agent targeting a cancer-promoting/sustaining molecule, (I)

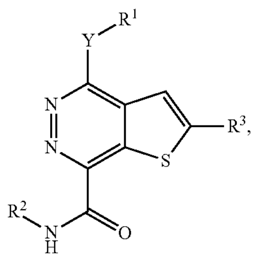

wherein Y is NH, O, S or $CH_2$;

$R^1$ is selected from the group consisting of

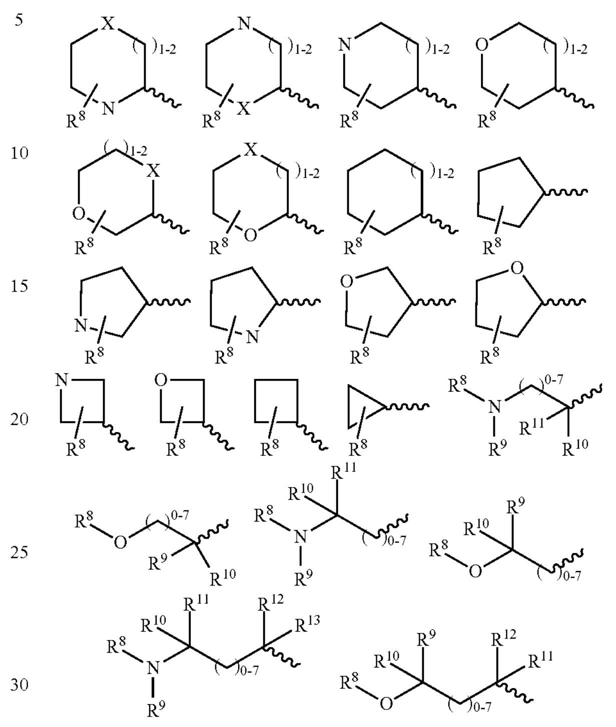

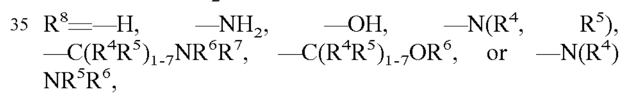

wherein X is $CH_2$, NH, S, or O, $R^8$=—H, —$NH_2$, —OH, —N($R^4$, $R^5$), —C($R^4R^5$)$_{1-7}$N$R^6R^7$, —C($R^4R^5$)$_{1-7}$O$R^6$, or —N($R^4$)N$R^5R^6$, wherein $R^4$, $R^5$, $R^6$, and $R^7$ are independently H, $C_1$-$C_6$ alkyl, $C_3$-$C_8$ cycloalkyl with or without nuclear heteroatoms such as O, S, and N; optionally substituted aryl, or optionally substituted heteroaromatic, $R^9$, $R^{10}$, $R^{11}$, $R^{12}$, and $R^{13}$ are independently H, $C_1$-$C_6$ alkyl, $C_3$-$C_8$ cycloalkyl with or without nuclear heteroatoms such as O, S or N; optionally substituted aryl, or optionally substituted heteroaromatic, $R^2$ is selected from a group consisting of H, OH, $NH_2$, $OR^{14}$, $NR^{14}R^{15}$, alkyl, aryl, heteroaryl, cycloalkyl, arylalkyl, heterocyclyl, heterocyclylalkyl, alkenyl, and alkynyl, wherein $R^{14}$ and $R^{15}$ are independently H, $C_1$-$C_6$ alkyl, $C_3$-$C_8$ cycloalkyl with or without nuclear heteroatoms such as O, S, N; optionally substituted aryl, or optionally substituted heteroaromatic, and $R^3$ is selected from a group consisting of H, alkyl, aryl, heteroaryl, cycloalkyl, arylalkyl, heterocyclyl, heterocyclylalkyl, alkenyl, and alkynyl.

In One embodiment, $R^3$ is selected from the group consisting of

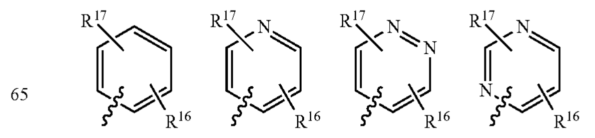

-continued

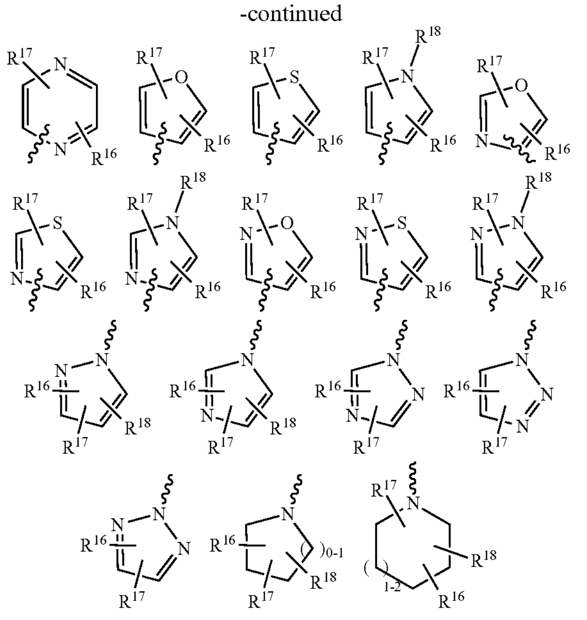

wherein $R^{16}$, $R^{17}$, and $R^{18}$ are independently H; F, Cl, Br, I; $C_1$-$C_8$ alkyl; $C_3$-$C_8$cycloalkyl without or with substitutions, wherein a substitution is selected from the group consisting of $C_1$-$C_8$alkyls, $C_3$-$C_8$ cycloalkyls, aryls, and heteroaryls; —$OR^{19}$; —$SR^{19}$; —$NR^{19}R^{20}$; —$S(O)R^{19}$; —$S(O)_2R^{19}$; —$S(O)_2NR^{19}R^{20}$; —$C(O)NR^{19}R^{20}$; —$N(R^{19})C(O)R^{20}$; —$N(R^{19})S(O)_2R^{20}$; —$N(R^{19})C(O)N(R^{20}R^{21})$; $N(R^{19})C(O)OR^{20}$; optionally substituted aryl, optionally substituted heteroaryl, optionally substituted aryalkyl, optionally substituted heterocyclyl, optionally substituted heteterocyclyl-alkyl; optionally substituted alkenyl, or optionally substituted alkynyl;

where $R^{19}$, $R^{20}$, and $R^{21}$ are independently H, $C_1$-$C_8$ alkyl, $C_3$-$C_8$ cycloalkyl, optionally substituted aryl, optionally substituted alkylaryl, or optionally substituted heteroaryl, or $R^{16}$, $R^{17}$, and $R^{21}$ are independently part of a fused ring containing 0-3 heteroatoms selected from N, O, and S.

In one embodiment, Y is NH. In one embodiment, Y is O. In one embodiment, Y is S.

In one embodiment, the compound of formula I is selected from the group consisting of 2-(4-fluorophenyl)-4-(3-piperidineamino)-thieno[2,3-d]pyridazine-7-carboxylic acid amide, 2-(4-chlorophenyl)-4-(3-piperidineamino)-thieno[2,3-d]pyridazine-7-carboxylic acid amide, 2-(4-bromophenyl)-4-(3-piperidineamino)-thieno[2,3-d]pyridazine-7-carboxylic acid amide, 2-(4-fluorophenyl)-4-(3-tetrahydropyran-amino)-thieno[2,3-d]pyridazine-7-carboxylic acid amide, 2-(4-chlorophenyl)-4-(3-tetrahydropyran-amino)-thieno[2,3-d]pyridazine-7-carboxylic acid amide, 2-(4-bromophenyl)-4-(3-tetrahydropyran-amino)-thieno[2,3-d]pyridazine-7-carboxylic acid amide, 2-(4-fluorophenyl)-4-(3-tetrahydrothiapyran-amino)-thieno[2,3-d]pyridazine-7-carboxylic acid amide, 2-(4-chlorophenyl)-4-(3-tetrahydrothiapyran-amino)-thieno[2,3-d]pyridazine-7-carboxylic acid amide, 2-(4-bromophenyl)-4-(3-tetrahydrothiapyran-amino)-thieno[2,3-d]pyridazine-7-carboxylic acid amide, 2-(4-chlorophenyl)-4-(2-piperidine-amino)-thieno[2,3-d]pyridazine-7-carboxylic acid amide, 2-(4-chlorophenyl)-4-(2-piperidine-amino)-thieno[2,3-d]pyridazine-7-carboxylic acid amide, 2-(4-chlorophenyl)-4-(S-3-piperidine-amino)-thieno[2,3-d]pyridazine-7-carboxylic acid amide, 2-(4-chlorophenyl)-4-(R-3-piperidine-amino)-thieno[2,3-d]pyridazine-7-carboxylic acid amide, 2-(4-chlorophenyl)-4-(3-piperidine-amino)-thieno[2,3-d]pyridazine-7-N-methyl-carboxylic acid amide, 2-(4-chlorophenyl)-4-(3-piperidine-amino)-thieno[2,3-d]pyridazine-7-N,N-dimethyl-carboxyli-c acid amide, 2-(4-chlorophenyl)-4-(3-tetrahydrothiapyran-amino)-thieno[2,3-d]pyridazine-7-N-methyl-carboxylic acid amide, 2-(4-chlorophenyl)-4-(3-tetrahydrothiapyran-amino)-thieno[2,3-d]pyridazine-7-N,N-dimethyl-carboxylic acid amide, 2-(4-chlorophenyl)-4-(3-tetrahydropyran-amino)-thieno[2,3-d]pyridazine-7-N-methyl-carboxylic acid amide, 2-(4-chlorophenyl)-4-(3-tetrahydropyran-amino)-thieno[2,3-d]pyridazine-7-N,N-dimethyl-carboxylic acid amide, 2-(4-fluorophenyl)-4-(3-tetrahydropyrrol-amino)-thieno[2,3-d]pyridazine-7-carboxylic acid amide, 2-(4-chlorophenyl)-4-(3-tetrahydropyrrol-amino)-thieno[2,3-d]pyridazine-7-carboxylic acid amide, 2-(4-bromophenyl)-4-(3-tetrahydropyrrol-amino)-thieno[2,3-d]pyridazine-7-carboxylic acid amide, 2-(4-fluorophenyl)-4-(3-tetrahydrofuran-amino)-thieno[2,3-d]pyridazine-7-carboxylic acid amide, 2-(4-chlorophenyl)-4-(3-tetrahydrofuran-amino)-thieno[2,3-d]pyridazine-7-carboxylic acid amide, 2-(4-bromophenyl)-4-(3-tetrahydrofuran-amino)-thieno[2,3-d]pyridazine-7-carboxylic acid amide, 2-(4-fluorophenyl)-4-(3-tetrahydrothieno-amino)-thieno[2,3-d]pyridazine-7-carboxylic acid amide, 2-(4-chlorophenyl)-4-(3-tetrahydrothieno-amino)-thieno[2,3-d]pyridazine-7-carboxylic acid amide, 2-(4-bromophenyl)-4-(3-tetrahydrothieno-amino)-thieno[2,3-d]pyridazine-7-carboxylic acid amide, 2-(4-chlorophenyl)-4-(2-tetrahydropyrrol-amino)-thieno[2,3-d]pyridazine-7-carboxylic acid amide, 2-(4-chlorophenyl)-4-(S-3-tetrahydropyrrol-amino)-thieno[2,3-d]pyridazine-7-carboxylic acid amide, 2-(4-chlorophenyl)-4-(R-3-tetrahydropyrrol-amino)-thieno[2,3-d]pyridazine-7-carboxylic acid amide, 2-(4-chlorophenyl)-4-(3-tetrahydropyrrol-amino)-thieno[2,3-d]pyridazine-7-N-methyl-carboxylic acid amide, 2-(4-chlorophenyl)-4-(3-tetrahydropyrrol-amino)-thieno[2,3-d]pyridazine-7-N,N-dimethyl-carboxylic acid amide, 2-(4-chlorophenyl)-4-(3-tetrahydrothieno-amino)-thieno[2,3-d]pyridazine-7-N-methyl-carboxylic acid amide, 2-(4-chlorophenyl)-4-(3-tetrahydrothieno-amino)-thieno[2,3-d]pyridazine-7-N,N-dimethyl-carboxylic acid amide, 2-(4-chlorophenyl)-4-(3-tetrahydrofuran-amino)-thieno[2,3-d]pyridazine-7-N-methyl-carboxylic acid amide, 2-(4-chlorophenyl)-4-(3-tetrahydrofuran-amino)-thieno[2,3-d]pyridazine-7-N,N-dimethyl-carboxylic acid amide, 2-(4-fluorophenyl)-4-(3-pyridin-amino)-thieno[2,3-d]pyridazine-7-carboxylic acid amide, 2-(4-chlorophenyl)-4-(3-pyridin-amino)-thieno[2,3-d]pyridazine-7-carboxylic acid amide, 2-(4-bromophenyl)-4-(3-pyridin-amino)-thieno[2,3-d]pyridazine-7-carboxylic acid amide, 2-(4-fluorophenyl)-4-(3-α-pyran-amino)-thieno[2,3-d]pyridazine-7-carboxylic acid amide, 2-(4-chlorophenyl)-4-(3-α-pyran-amino)-thieno[2,3-d]pyridazine-7-carboxylic acid amide, 2-(4-bromophenyl)-4-(3-α-pyran-amino)-thieno[2,3-d]pyridazine-7-carboxylic acid amide, 2-(4-fluorophenyl)-4-(3-α-thiapyran-amino)-thieno[2,3-d]pyridazine-7-carboxylic acid amide,
2-(4-chlorophenyl)-4-(3-α-thiapyran-amino)-thieno[2,3-d]pyridazine-7-carboxylic acid amide,
2-(4-bromophenyl)-4-(3-α-thiapyran-amino)-thieno[2,3-d]pyridazine-7-carboxylic acid amide,
2-(4-chlorophenyl)-4-(2-pyridin-amino)-thieno[2,3-d]pyridazine-7-carboxylic acid amide
2-(4-chlorophenyl)-4-(4-pyridin-amino)-thieno[2,3-d]pyridazine-7-carboxylic acid amide
2-(4-chlorophenyl)-4-(S-3-pyridin-amino)-thieno[2,3-d]pyridazine-7-carboxylic acid amide,
2-(4-chlorophenyl)-4-(R-3-pyridin-amino)-thieno[2,3-d]pyridazine-7-carboxylic acid amide,
2-(4-chlorophenyl)-4-(3-pyridin-amino)-thieno[2,3-d]pyridazine-7-N-methyl-carboxylic acid amide,
2-(4-chlorophenyl)-4-(3-pyridin-amino)-thieno[2,3-d]pyridazine-7-N,N-dimethyl-carboxylic acid amide,
2-(4-chlorophenyl)-4-(3-thiapyran-amino)-thieno[2,3-d]pyridazine-7-N-methyl-carboxylic acid amide,
2-(4-chlorophenyl)-4-(3-thiapyran-amino)-thieno[2,3-d]pyridazine-7-N,N-dimethyl-carboxylic acid amide,
2-(4-chlorophenyl)-4-(3-pyran-amino)-thieno[2,3-d]pyridazine-7-N-methyl-carboxylic acid amide,
2-(4-chlorophenyl)-4-(3-pyran-amino)-thieno[2,3-d]pyridazine-7-N,N-dimethyl-carboxylic acid amide,
2-(4-fluorophenyl)-4-(3-pyrrol-amino)-thieno[2,3-d]pyridazine-7-carboxylic acid amide,
2-(4-chlorophenyl)-4-(3-pyrrol-amino)-thieno[2,3-d]pyridazine-7-carboxylic acid amide,
2-(4-bromophenyl)-4-(3-pyrrol-amino)-thieno[2,3-d]pyridazine-7-carboxylic acid amide,
2-(4-fluorophenyl)-4-(3-furan-amino)-thieno[2,3-d]pyridazine-7-carboxylic acid amide,
2-(4-chlorophenyl)-4-(3-furan-amino)-thieno[2,3-d]pyridazine-7-carboxylic acid amide,
2-(4-bromophenyl)-4-(3-furan-amino)-thieno[2,3-d]pyridazine-7-carboxylic acid amide,
2-(4-fluorophenyl)-4-(3-thieno-amino)-thieno[2,3-d]pyridazine-7-carboxylic acid amide,
2-(4-chlorophenyl)-4-(3-thieno-amino)-thieno[2,3-d]pyridazine-7-carboxylic acid amide,
2-(4-bromophenyl)-4-(3-thieno-amino)-thieno[2,3-d]pyridazine-7-carboxylic acid amide,
2-(4-chlorophenyl)-4-(2-pyrrol-amino)-thieno[2,3-d]pyridazine-7-carboxylic acid amide,
2-(4-chlorophenyl)-4-(S-3-pyrrol-amino)-thieno[2,3-d]pyridazine-7-carboxylic acid amide,
2-(4-chlorophenyl)-4-(R-3-pyrrol-amino)-thieno[2,3-d]pyridazine-7-carboxylic acid amide,
2-(4-chlorophenyl)-4-(3-pyrrol-amino)-thieno[2,3-d]pyridazine-7-N-methyl-carboxylic acid amide,
2-(4-chlorophenyl)-4-(3-pyrrol-amino)-thieno[2,3-d]pyridazine-7-N,N-dimethyl-carboxylic acid amide,
2-(4-chlorophenyl)-4-(3-thieno-amino)-thieno[2,3-d]pyridazine-7-N-methyl-carboxylic acid amide,
2-(4-chlorophenyl)-4-(3-thieno-amino)-thieno[2,3-d]pyridazine-7-N,N-dimethyl-carboxylic acid amide,
2-(4-chlorophenyl)-4-(3-furan-amino)-thieno[2,3-d]pyridazine-7-N-methyl-carboxylic acid amide,
2-(4-chlorophenyl)-4-(3-furan-amino)-thieno[2,3-d]pyridazine-7-N,N-dimethyl-carboxylic acid amide,
2-(3-fluorophenyl)-4-(3-piperidineamino)-thieno[2,3-d]pyridazine-7-carboxylic acid amide,
2-(3-chlorophenyl)-4-(3-piperidineamino)-thieno[2,3-d]pyridazine-7-carboxylic acid amide,
2-(3-bromophenyl)-4-(3-piperidineamino)-thieno[2,3-d]pyridazine-7-carboxylic acid amide,
2-(3-chlorophenyl)-4-(3-piperibine-amino)-thieno[2,3-d]pyridazine-7-N,N-dimethyl-carboxylic acid amide,
2-(3-chlorophenyl)-4-(3-tetrahydrothiapyran-amino)-thieno[2,3-d]pyridazine-7-N-methyl-carboxylic acid amide,
2-(3-chlorophenyl)-4-(3-tetrahydrothiapyran-amino)-thieno[2,3-d]pyridazine-7-N,N-dimethyl-carboxylic acid amide,
2-(3-chlorophenyl)-4-(3-tetrahydropyran-amino)-thieno[2,3-d]pyridazine-7-N-methyl-carboxylic acid amide,
2-(3-chlorophenyl)-4-(3-tetrahydropyran-amino)-thieno[2,3-d]pyridazine-7-N,N-dimethyl-carboxylic acid amide,
2-(3-fluorophenyl)-4-(3-tetrahydropyrrol-amino)-thieno[2,3-d]pyridazine-7-carboxylic acid amide,
2-(3-chlorophenyl)-4-(3-tetrahydropyrrol-amino)-thieno[2,3-d]pyridazine-7-carboxylic acid amide,
2-(3-bromophenyl)-4-(3-tetrahydropyrrol-amino)-thieno[2,3-d]pyridazine-7-carboxylic acid amide,
2-(3-fluorophenyl)-4-(3-tetrahydrofuran-amino)-thieno[2,3-d]pyridazine-7-carboxylic acid amide,
2-(3-chlorophenyl)-4-(3-tetrahydrofuran-amino)-thieno[2,3-d]pyridazine-7-carboxylic acid amide,
2-(3-bromophenyl)-4-(3-tetrahydrofuran-amino)-thieno[2,3-d]pyridazine-7-carboxylic acid amide,
2-(3-fluorophenyl)-4-(3-tetrahydrothieno-amino)-thieno[2,3-d]pyridazine-7-carboxylic acid amide,
2-(3-chlorophenyl)-4-(3-tetrahydrothieno-amino)-thieno[2,3-d]pyridazine-7-carboxylic acid amide,
2-(3-bromophenyl)-4-(3-tetrahydrothieno-amino)-thieno[2,3-d]pyridazine-7-carboxylic acid amide,
2-(3-chlorophenyl)-4-(2-tetrahydropyrrol-amino)-thieno[2,3-d]pyridazine-7-carboxylic acid amide,
2-(3-chlorophenyl)-4-(S-3-tetrahydropyrrol-amino)-thieno[2,3-d]pyridazine-7-carboxylic acid amide,
2-(3-chlorophenyl)-4-(R-3-tetrahydropyrrol-amino)-thieno[2,3-d]pyridazine-7-carboxylic acid amide,
2-(3-chlorophenyl)-4-(3-tetrahydropyrrol-amino)-thieno[2,3-d]pyridazine-7-N-methyl-carboxylic acid amide,
2-(3-chlorophenyl)-4-(3-tetrahydropyrrol-amino)-thieno[2,3-d]pyridazine-7-N,N-dimethyl-carboxylic acid amide,
2-(3-fluorophenyl)-4-(3-pyridin-amino)-thieno[2,3-d]pyridazine-7-carboxylic acid amide,
2-(3-chlorophenyl)-4-(3-pyridin-amino)-thieno[2,3-d]pyridazine-7-carboxylic acid amide,
2-(3-bromophenyl)-4-(3-pyridin-amino)-thieno[2,3-d]pyridazine-7-carboxylic acid amide,
2-(3-fluorophenyl)-4-(3-α-pyran-amino)-thieno[2,3-d]pyridazine-7-carboxylic acid amide,
2-(3-chlorophenyl)-4-(3-α-pyran-amino)-thieno[2,3-d]pyridazine-7-carboxylic acid amide,
2-(3-bromophenyl)-4-(3-α-pyran-amino)-thieno[2,3-d]pyridazine-7-carboxylic acid amide,
2-(3-fluorophenyl)-4-(3-α-thiapyran-amino)-thieno[2,3-d]pyridazine-7-carboxylic acid amide,
2-(3-chlorophenyl)-4-(3-α-thiapyran-amino)-thieno[2,3-d]pyridazine-7-carboxylic acid amide,
2-(3-bromophenyl)-4-(3-α-thiapyran-amino)-thieno[2,3-d]pyridazine-7-carboxylic acid amide,
2-(3-chlorophenyl)-4-(2-pyridin-amino)-thieno[2,3-d]pyridazine-7-carboxylic acid amide,
2-(3-chlorophenyl)-4-(4-pyridin-amino)-thieno[2,3-d]pyridazine-7-carboxylic acid amide,
2-(3-chlorophenyl)-4-(S-3-pyridin-amino)-thieno[2,3-d]pyridazine-7-carboxylic acid amide,
2-(3-chlorophenyl)-4-(R-3-pyridin-amino)-thieno[2,3-d]pyridazine-7-carboxylic acid amide, 2-(3-chlorophenyl)-4-(3-pyridin-amino)-thieno[2,3-d] pyridazine-7-N-methyl-carboxylic acid amide,
2-(3-chlorophenyl)-4-(3-pyridin-amino)-thieno[2,3-d] pyridazine-7-N,N-dimethyl-carboxylic acid amide,
2-(3-chlorophenyl)-4-(3-thiapyran-amino)-thieno[2,3-d] pyridazine-7-N-methyl-carboxylic acid amide,
2-(3-chlorophenyl)-4-(3-thiapyran-amino)-thieno[2,3-d] pyridazine-7-N,N-dimethyl-carboxylic acid amide,
2-(3-chlorophenyl)-4-(3-pyran-amino)-thieno[2,3-d] pyridazine-7-N-methyl-carboxylic acid amide,
2-(3-chlorophenyl)-4-(3-pyran-amino)-thieno[2,3-d] pyridazine-7-N,N-dimethyl-carboxylic acid amide,
2-(3-fluorophenyl)-4-(3-pyrrol-amino)-thieno[2,3-d] pyridazine-7-carboxylic acid amide,
2-(3-chlorophenyl)-4-(3-pyrrol-amino)-thieno[2,3-d] pyridazine-7-carboxylic acid amide,
2-(3-bromophenyl)-4-(3-pyrrol-amino)-thieno[2,3-d] pyridazine-7-carboxylic acid amide,
2-(3-fluorophenyl)-4-(3-furan-amino)-thieno[2,3-d] pyridazine-7-carboxylic acid amide,
2-(3-chlorophenyl)-4-(3-furan-amino)-thieno[2,3-d] pyridazine-7-carboxylic acid amide,
2-(3-bromophenyl)-4-(3-furan-amino)-thieno[2,3-d] pyridazine-7-carboxylic acid amide,
2-(3-fluorophenyl)-4-(3-thieno-amino)-thieno[2,3-d] pyridazine-7-carboxylic acid amide,
2-(3-chlorophenyl)-4-(3-thieno-amino)-thieno[2,3-d] pyridazine-7-carboxylic acid amide,
2-(3-bromophenyl)-4-(3-thieno-amino)-thieno[2,3-d] pyridazine-7-carboxylic acid amide,
2-(3-chlorophenyl)-4-(2-pyrrol-amino)-thieno[2,3-d] pyridazine-7-carboxylic acid amide,
2-(3-chlorophenyl)-4-(S-3-pyrrol-amino)-thieno[2,3-d] pyridazine-7-carboxylic acid amide,
2-(3-chlorophenyl)-4-(R-3-pyrrol-amino)-thieno[2,3-d] pyridazine-7-carboxylic acid amide,
2-(3-chlorophenyl)-4-(3-pyrrol-amino)-thieno[2,3-d] pyridazine-7-N-methyl-carboxylic acid amide,
2-(3-chlorophenyl)-4-(3-pyrrol-amino)-thieno[2,3-d] pyridazine-7-N,N-dimethyl-carboxylic acid amide,
2-(3-chlorophenyl)-4-(3-thieno-amino)-thieno[2,3-d] pyridazine-7-N-methyl-carboxylic acid amide,
2-(3-chlorophenyl)-4-(3-thieno-amino)-thieno[2,3-d] pyridazine-7-N,N-dimethyl-carboxylic acid amide,
2-(3-chlorophenyl)-4-(3-furan-amino)-thieno[2,3-d] pyridazine-7-N-methyl-carboxylic acid amide,
2-(3-chlorophenyl)-4-(3-furan-amino)-thieno[2,3-d] pyridazine-7-N,N-dimethyl-carboxylic acid amide,
2-(3-fluorophenyl)-4-(3-piperidinyloxy)-thieno[2,3-d] pyridazine-7-carboxylic acid amide,
2-(3-fluorophenyl)-4-(3-piperidinylthio)-thieno[2,3-d] pyridazine-7-carboxylic acid amide,2-(4-fluorophenyl)-4-(3-piperidinemethyl)-thieno[2,3-d] pyridazinyl-7-formamide;
2-(4-chlorophenyl)-4-(3-piperidinemethyl)-thieno[2,3-d] pyridazinyl-7-formamide;
2-(4-bromophenyl)-4-(3-piperidinemethyl)-thieno[2,3-d] pyridazinyl-7-formamide;
2-(4-fluorophenyl)-4-(3-tetrahydropyranmethyl)-thieno[2,3-d]pyridazinyl-7-formamide;
2-(4-chlorophenyl)-4-(3-tetrahydropyranmethyl)-thieno[2,3-d]pyridazinyl-7-formamide;
2-(4-bromophenyl)-4-(3-tetrahydropyranmethyl)-thieno[2,3-d]pyridazinyl-7-formamide;
2-(4-fluorophenyl)-4-(3-tetrahydrothiapyranmethyl)-thieno [2,3-d]pyridazinyl-7-formamide;
2-(4-chlorophenyl)-4-(3-tetrahydrothiapyranmethyl)-thieno [2,3-d]pyridazinyl-7-formamide;
2-(4-bromophenyl)-4-(3-tetrahydrothiapyranmethyl)-thieno [2,3-d]pyridazinyl-7-formamide;
2-(4-chlorophenyl)-4-(2-piperidinemethyl)-thieno[2,3-d] pyridazinyl-7-formamide;
2-(4-chlorophenyl)-4-(4-piperidinemethyl)-thieno[2,3-d] pyridazinyl-7-formamide;
2-(4-chlorophenyl)-4-(S-3-piperidinemethyl)-thieno[2,3-d] pyridazinyl-7-formamide;
2-(4-chlorophenyl)-4-(R-3-piperidinemethyl)-thieno[2,3-d] pyridazinyl-7-formamide;
2-(4-chlorophenyl)-4-(3-piperidinemethyl)-thieno [2,3-d] pyridazinyl-7-N-methyl-formamide;
2-(4-chlorophenyl)-4-(3-piperidinemethyl)-thieno[2,3-d] pyridazinyl-7-N,N-dimethyl-7-formamide;
2-(4-chlorophenyl)-4-(3-tetrahydrothiapyranmethyl)-thieno [2,3-d]pyridazinyl-7-N-methyl-formamide;
2-(4-chlorophenyl)-4-(3-tetrahydrothiapyranmethyl)-thieno [2,3-d]pyridazinyl-7-N,N-dimethyl-7-formamide;
2-(4-chlorophenyl)-4-(3-tetrahydropyranmethyl)-thieno[2,3-d]pyridazinyl-7-N-methyl-formamide;
2-(4-chlorophenyl)-4-(3-tetrahydropyranmethyl)-thieno[2,3-d]pyridazinyl-7-N,N-dimethyl-7-formamide;
2-(4-fluorophenyl)-4-(3-pyrrolidinemethyl)-thieno[2,3-d] pyridazinyl-7-formamide;
2-(4-chlorophenyl)-4-(3-pyrrolidinemethyl)-thieno[2,3-d] pyridazinyl-7-formamide;
2-(4-bromophenyl)-4-(3-pyrrolidinemethyl)-thieno[2,3-d] pyridazinyl-7-formamide;
2-(4-fluorophenyl)-4-(3-tetrahydrofuranmethyl)-thieno[2,3-d]pyridazinyl-7-formamide;
2-(4-chlorophenyl)-4-(3-tetrahydrofuranmethyl)-thieno[2,3-d]pyridazinyl-7-formamide;
2-(4-bromophenyl)-4-(3-tetrahydrofuranmethyl)-thieno[2,3-d]pyridazinyl-7-formamide;
2-(4-fluorophenyl)-4-(3-tetrahydrothiophenemethyl)-thieno [2,3-d]pyridazinyl-7-formamide;
2-(4-chlorophenyl)-4-(3-tetrahydrothiophenemethyl)-thieno [2,3-d]pyridazinyl-7-formamide;
2-(4-bromophenyl)-4-(3-tetrahydrothiophenemethyl)-thieno [2,3-d]pyridazinyl-7-formamide;
2-(4-chlorophenyl)-4-(3-pyrrolidinemethyl)-thieno[2,3-d] pyridazinyl-7-formamide;
2-(4-chlorophenyl)-4-(S-3-pyrrolidinemethyl)-thieno[2,3-d] pyridazinyl-7-formamide;
2-(4-chlorophenyl)-4-(R-3-pyrrolidinemethyl)-thieno[2,3-d]pyridazinyl-7-formamide;
2-(4-chlorophenyl)-4-(3-pyrrolidinemethyl)-thieno[2,3-d] pyridazinyl-7-N-methyl-formamide;
2-(4-chlorophenyl)-4-(3-pyrrolidinemethyl)-thieno[2,3-d] pyridazinyl-7-N,N-dimethyl-formamide;
2-(4-chlorophenyl)-4-(3-tetrahydrothiophenemethyl)-thieno [2,3-d]pyridazinyl-7-N-methyl-formamide;
2-(4-chlorophenyl)-4-(3-tetrahydrothiophenemethyl)-thieno [2,3-d]pyridazinyl-7-N,N-dimethyl-formamide;
2-(4-chlorophenyl)-4-(3-tetrahydrofuranmethyl)-thieno[2,3-d]pyridazinyl-7-N-methyl-formamide;
2-(4-chlorophenyl)-4-(3-tetrahydrofuranmethyl)-thieno[2,3-d]pyridazinyl-7-N,N-dimethyl-formamide;
2-(4-fluorophenyl)-4-(3-pyridinemethyl)-thieno[2,3-d] pyridazinyl-7-formamide;
2-(4-chlorophenyl)-4-(3-pyridinemethyl)-thieno[2,3-d] pyridazinyl-7-formamide;
2-(4-bromophenyl)-4-(3-pyridinemethyl)-thieno[2,3-d] pyridazinyl-7-formamide;

2-(4-fluorophenyl)-4-(3-α-pyranmethyl)-thieno[2,3-d] pyridazinyl-7-formamide;
2-(4-chlorophenyl)-4-(3-α-pyranmethyl)-thieno[2,3-d] pyridazinyl-7-formamide;
2-(4-bromophenyl)-4-(3-α-pyranmethyl)-thieno[2,3-d] pyridazinyl-7-formamide;
2-(4-fluorophenyl)-4-(3-α-thiopyranmethyl)-thieno[2,3-d] pyridazinyl-7-formamide;
2-(4-chlorophenyl)-4-(3-α-thiopyranmethyl)-thieno[2,3-d] pyridazinyl-7-formamide;
2-(4-bromophenyl)-4-(3-α-thiopyranmethyl)-thieno[2,3-d] pyridazinyl-7-formamide;
2-(4-chlorophenyl)-4-(2-pyridinemethyl)-thieno[2,3-d] pyridazinyl-7-formamide;
2-(4-chlorophenyl)-4-(4-pyridinemethyl)-thieno[2,3-d] pyridazinyl-7-formamide;
2-(4-chlorophenyl)-4-(3-pyridinemethyl)-thieno[2,3-d] pyridazinyl-7-N-methyl formamide;
2-(4-chlorophenyl)-4-(3-pyridinemethyl)-thieno[2,3-d] pyridazinyl-7-N,N-dimethyl formamide;
2-(4-chlorophenyl)-4-(3-thiopyranylmethyl)-thieno[2,3-d] pyridazinyl-7-N-methyl formamide;
2-(4-chlorophenyl)-4-(3-thiopyranylmethyl)-thieno[2,3-d] pyridazinyl-7-N,N-dimethyl formamide;
2-(4-chlorophenyl)-4-(3-pyranmethyl)-thieno[2,3-d] pyridazinyl-7-N-methyl formamide;
2-(4-chlorophenyl)-4-(3-pyranmethyl)-thieno[2,3-d] pyridazinyl-7-N,N-dimethyl formamide;
2-(4-fluorophenyl)-4-(3-pyrrolemethyl)-thieno[2,3-d] pyridazinyl-7-formamide;
2-(4-chlorophenyl)-4-(3-pyrrolemethyl)-thieno[2,3-d] pyridazinyl-7-formamide;
2-(4-bromophenyl)-4-(3-pyrrolemethyl)-thieno[2,3-d] pyridazinyl-7-formamide;
2-(4-fluorophenyl)-4-(3-furanmethyl)-thieno[2,3-d] pyridazinyl-7-formamide;
2-(4-chlorophenyl)-4-(3-furanmethyl)-thieno[2,3-d] pyridazinyl-7-formamide;
2-(4-bromophenyl)-4-(3-furanmethyl)-thieno[2,3-d] pyridazinyl-7-formamide;
2-(4-fluorophenyl)-4-(3-thiaphenemethyl)-thieno[2,3-d] pyridazinyl-7-formamide;
2-(4-chlorophenyl)-4-(3-thiaphenemethyl)-thieno[2,3-d] pyridazinyl-7-formamide;
2-(4-bromophenyl)-4-(3-thiaphenemethyl)-thieno[2,3-d] pyridazinyl-7-formamide;
2-(4-chlorophenyl)-4-(2-pyrrolemethyl)-thieno[2,3-d] pyridazinyl-7-formamide;
2-(4-chlorophenyl)-4-(3-pyrrolemethyl)-thieno[2,3-d] pyridazinyl-7-N-methyl formamide;
2-(4-chlorophenyl)-4-(3-pyrrolemethyl)-thieno[2,3-d] pyridazinyl-7-N,N-dimethyl formamide;
2-(4-chlorophenyl)-4-(3-thiaphenemethyl)-thieno[2,3-d] pyridazinyl-7-N-methyl formamide;
2-(4-chlorophenyl)-4-(3-thiaphenemethyl)-thieno[2,3-d] pyridazinyl-7-N,N-dimethyl formamide;
2-(4-chlorophenyl)-4-(3-furanmethyl)-thieno[2,3-d] pyridazinyl-7-N-methyl formamide;
2-(4-chlorophenyl)-4-(3-furanmethyl)-thieno[2,3-d] pyridazinyl-7-N,N-dimethyl formamide; and
2-(3,5-dichlorophenyl)-4-(3-piperidinemethyl)-thieno[2,3-d]pyridazinyl-7-formamide.

The PARP inhibitor may be a compound having inhibitory effect on PARP activity. In certain embodiments, the PARP inhibitor may be Olaparib, Rucaparib, Niraparib, or Talazoparib.

In one embodiment, the cancer is a solid cancer selected from the group consisting of lung, prostate, ovarian, brain, breast, skin, bladder, colon, gastrointestinal, head and neck, gastric, pancreas, neurologic, renal, and liver cancer. In one embodiment, the cancer is breast cancer. In one embodiment, the cancer is ovarian adenocarcinoma.

In one embodiment, the cancer is a hematological cancer selected from the group consisting of lymphocytic leukemia, myeloid leukemia, non-Hodgkin lymphoma, and Hodgkin lymphoma.

In certain embodiments, the cancer is a BRCA-mutant cancer, e.g., a BRCA-mutant breast cancer, or a BRCA-mutant ovarian cancer.

The compound of formula I and the PARP inhibitor may be administered concurrently as a single composition in a pharmaceutically acceptable carrier, or concurrently as separate compositions. They can also be administered sequentially.

The present disclosure also discloses the use of the compound of formula I in combination with the PARP inhibitor in treatment of a cancer disease.

The exemplary combined use of the disclosure provides enhanced inhibitory effects on tumor cells. In particular, the CHK inhibitor and the PARP inhibitor synergistically induced tumor cell death in the disclosure.

In a second aspect, the present disclosure discloses a method for treating a cancer, comprising administering a subject in need thereof a therapeutically effective amount of a compound of formula I, or the pharmaceutically acceptable salt thereof, in combination with i) a PARP inhibitor, and ii) a chemotherapeutic agent.

The PARP inhibitor may be a compound having inhibitory effect on PARP activity. In certain embodiments, the PARP inhibitor may be Olaparib, Rucaparib, Niraparib, or Talazoparib.

The chemotherapeutic agent suitable for the present invention may be cisplatin, pemetrexed, gemcitabine, cytarabine, hydroxycarbamide, temozolomide, irinotecan, cyclophosphamide, mitoxantrone, etoposide, folinic acid, fludarabine, fluorouracil, or a combination thereof.

In one embodiment, the cancer is a solid cancer selected from the group consisting of lung, prostate, ovarian, brain, breast, skin, bladder, colon, gastrointestinal, head and neck, gastric, pancreas, neurologic, renal, and liver cancer. In one embodiment, the cancer is breast cancer. In one embodiment, the cancer is ovarian adenocarcinoma.

In one embodiment, the cancer is a hematological cancer selected from the group consisting of lymphocytic leukemia, myeloid leukemia, non-Hodgkin lymphoma, and Hodgkin lymphoma.

In certain embodiments, the cancer is a BRCA-mutant cancer, e.g., a BRCA-mutant breast cancer, or a BRCA-mutant ovarian cancer.

The compound of formula I, the PARP inhibitor and the chemotherapeutic agent may be administered concurrently as a single composition in a pharmaceutically acceptable carrier, or concurrently as separate compositions. They can also be administered sequentially.

The present disclosure also discloses the use of the compound of formula I in combination with the PARP inhibitor and the chemotherapeutic agent in treatment of a cancer disease.

The exemplary combined use of the disclosure provides enhanced inhibitory effects on tumor cells. In particular, the CHK inhibitor, the PARP inhibitor and the chemotherapeutic agent synergistically induced tumor cell death in the present disclosure.

Other features and advantages of the instant disclosure, literally described and their equivalents understood by those ordinarily skilled in the art, will be apparent from the following drawings, detailed description and examples, as well as claims, which should not be construed as limiting. The contents of all publications, references, Genbank entries, patents and published patent applications cited throughout this application are expressly incorporated herein by reference.

DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
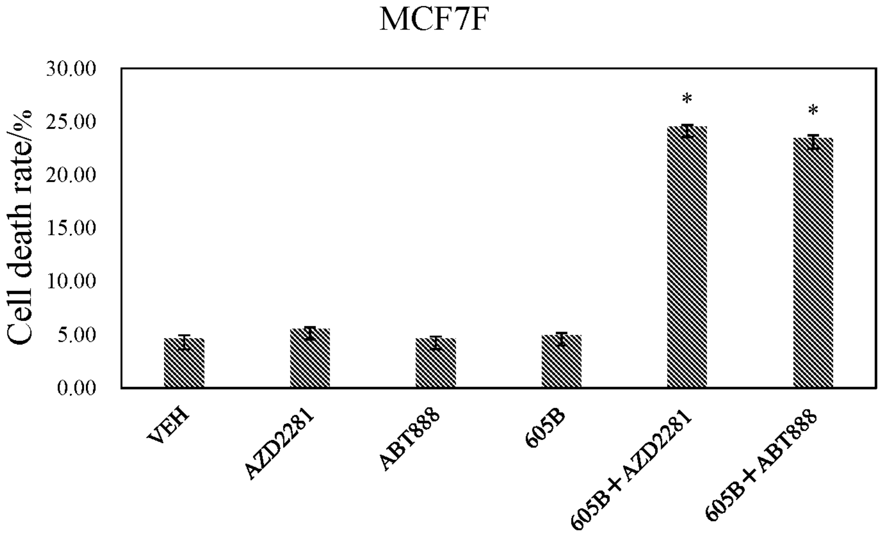
FIG. 1 is a column graph showing the death rates of MCF7F cells treated with Compound 605B, AZD2281, ABT888, 605B+AZD2281, and 605B+ABT888, respectively.

Before particular embodiments of the present disclosure are disclosed and described, it is to be understood that this disclosure is not limited to the particular process and materials disclosed herein as such may vary to some degree. It is also to be understood that the terminology used herein is used for the purpose of describing particular embodiments only and is not intended to be limiting, as the scope of the present disclosure will be defined only by the appended claims and equivalents thereof.

The singular forms "a," "an," and "the" include plural referents unless the context clearly dictates otherwise.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C═C double bonds, C═N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure.

As referred to herein, the term "substituted" means that at least one hydrogen atom is replaced with a non-hydrogen group, provided that normal valencies are maintained and that the substitution results in a stable compound.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $—SO_2NH_2$, substituted sulfonamido, nitro, cyano, carboxy, carbamyl, e.g. $—CONH_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Exemplary alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_1$-$C_6$ alkoxy" (or alkyloxy), is intended to include $C_1$, $C_2$, $C_3$, $C_4$, $C_5$, and C alkoxy groups. Exemplary alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the disclosure, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

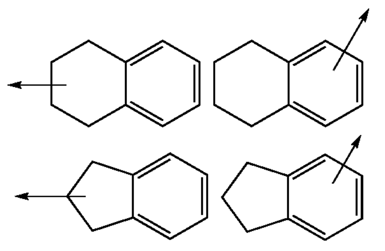

Arrowed lines drawn from the ring system indicate that the bond may be attached to any of the suitable ring atoms.

The term "cycloalkyl" refers to cyclized alkyl groups. $C_3$-$C_6$ cycloalkyl is intended to include $C_3$, $C_4$, $C_5$, and $C_6$ cycloalkyl groups. Exemplary cycloalkyl groups include, but are not limited to, cyclopropyl, cyclobutyl, cyclopentyl, cyclohexyl, and norbornyl.

Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Exemplary cycloalkenyl groups include, but are not limited to, cyclobutenyl, cyclopentenyl, and cyclohexenyl.

As used herein, the term "heterocycle," "heterocyclyl," or "heterocyclic group" is intended to mean a stable 4-, 5-, or 6-membered monocyclic that is saturated, partially unsaturated, or fully unsaturated, and that contains carbon atoms and 1, 2, 3 or 4 nitrogen, oxygen or other non-carbon atoms.

In cases wherein there are nitrogen atoms (e.g., amines) on compounds of the present disclosure, these may be converted to N-oxides by treatment with an oxidizing agent (e.g., mCPBA and/or hydrogen peroxides) to afford other compounds of this disclosure. Thus, shown and claimed nitrogen atoms are considered to cover both the shown nitrogen and its N-oxide (N->0) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: The Science and Practice of Pharmacy, 22nd Edition, Allen, L. V. Jr., Ed.; Pharmaceutical Press, London, UK (2012), the disclosure of which is hereby incorporated by reference.

As used herein, the term "effective amount" means that amount of a drug or pharmaceutical agent, i.e., a compound of the disclosure, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "parenteral" includes subcutaneous, intradermal, intravenous, intramuscular, intraarticular, intraarterial, synovial, intrasternal, intracranial, intramuscular or infusion.

Compound of Formula I

The compounds of formula I are disclosed in WO2009/092278 and WO2011/035077 as CHK inhibitors. They have direct anti-tumor effects and can sensitize other DNA-damaging drugs. The synthesis scheme and the function tests of these compounds are also specifically described in the two international patent applications.

The exemplary compounds include

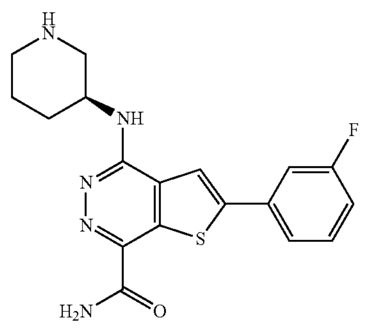 [SMILES: NC(=O)c1nnc(N[C@H]2CCCNC2)c2cc(-c3cccc(F)c3)sc12]

(2-(3-fluorophenyl)-4-(3-piperidineamino)-thieno[2,3-d] pyridazine-7-carboxylic acid amide, referred to as Compound 605B in Examples 1 to 3),

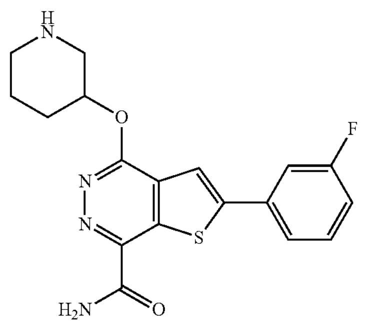 [SMILES: NC(=O)c1nnc(SC2CCCNC2)c2cc(-c3cccc(F)c3)sc12]

(2-(3-fluorophenyl)-4-(3-piperidinyloxy)-thieno[2,3-d] pyridazine-7-carboxylic acid amide),

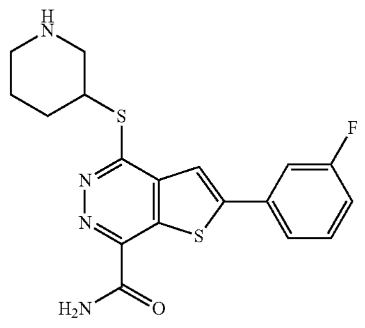

(2-(3-fluorophenyl)-4-(3-piperidinylthio)-thieno[2,3-d] pyridazine-7-carboxylic acid amide),

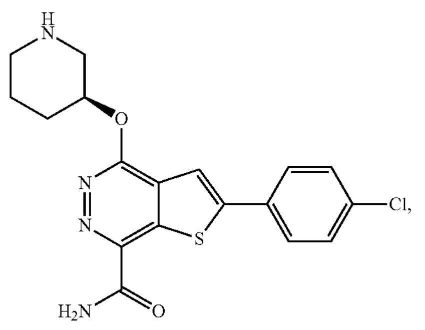

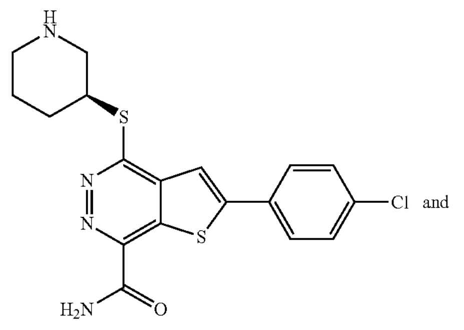

and

-continued

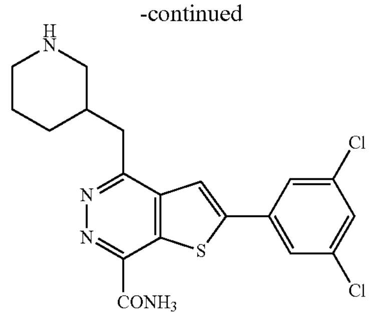

(2-(3,5-dichlorophenyl)-4-(3-piperidinemethyl)-thieno[2,3-d]pyridazinyl-7-formamide).

PARP Inhibitor

PARP is a family of proteins that catalyze the transfer of ADP-ribose to target proteins. It plays an important role in several cellular processes, including transcription, replication, recombination and DNA repair, among which DNA repair is of particular interest where PARP detects and initiates an immediate cellular response to single-strand DNA breaks (SSB).

Certain tumors defective in homologous recombination repair (HRR) mechanisms, e.g., BRCA-mutant cancers, may rely on PARP-mediated DNA repair for survival, and thus sensitive to PARP inhibition. In particular, PARP inhibitors impair SSB repair, leading to double-strand DNA breaks (DSB). When such DSBs cannot be efficiently repaired by HRR, cancer cell death may occur (Martin S A, et al., (2008) *Curr Opin Genet Dev* 18:80-86). The PARP inhibitors are usually used to increase tumor sensitivity to DNA-damaging agents.

Researches have further found that ATR/CHK1 pathway prevents DNA DSB, and inhibition of this pathway might increase reliance on HRR. Such finding may serve as the basis for the combined use of a CHK1 inhibitor and a PARP inhibitor in treatment of cancers, especially BRCA-mutant cancers. In deed, studies have shown that the combined use of a certain CHK inhibitor with a certain PARP inhibitor resulted in tumor regression in BRCA-mutant ovarian cancer models (Hyoung Kim et al., (2017) Clin. Cancer Res. 23(12):3097-3108).

Chemotherapeutic Agent

The chemotherapeutic agent herein refers to a powerful chemical that kills fast-growing cells in the body. Such an agent is usually used to treat cancers, as cancer cells grow and divide faster than other cells.

Chemotherapeutic agents for cancer treatment include, but not limited to, cisplatin, pemetrexed, gemcitabine, cytarabine, hydroxycarbamide, temozolomide, irinotecan, cyclophosphamide, mitoxantrone, etoposide, folinic acid, fludarabine, and fluorouracil.

Gemcitabine, a chemotherapy medication used in treatment of a number of types of cancers, is a ribonucleotide reductase inhibitor that leads to dNTP depletion and fork stalling, blocking the formation of new DNAs. It was first approved in 1995 for medical use, and is now used as a first-line treatment alone for pancreatic cancer, and in combination with cisplatin for advanced or metastatic bladder cancer and advanced or metastatic non-small cell lung cancer. It is also used as a second-line treatment in combination with carboplatin for ovarian cancer and in combination with paclitaxel for breast cancer that is metastatic or cannot be surgically removed. Gemcitabine use may cause side effects such as bone marrow suppression, liver and kidney problems, nausea, fever, and hair loss.

Cisplatin is another chemotherapy medication commonly used in treatment of a number of cancers. It was discovered in 1845 and put into medical use in 1978. It works by binding to DNA and thus inhibiting DNA replication, and is used to treat sarcomas, SCLC, ovarian cancer and etc.

Combination Therapy

The compounds of formula I, as the CHK inhibitor, may be used in combination with i) a PARP inhibitor, and optionally (ii) a chemotherapeutic agent, to gain a better anti-cancer effect and/or a lower toxicity to human body.

The compound of formula I and the PARP inhibitor may be administered concurrently as a single composition in a pharmaceutically acceptable carrier, or concurrently as separate compositions. They can also be administered sequentially.

In other embodiments, the compound of formula I, the chemotherapeutic agent, and the PARP inhibitor may be administered concurrently as a single composition in a pharmaceutically acceptable carrier, or concurrently as separate compositions. They can also be administered sequentially.

The combination therapy of the present disclosure may be used to treat a cancer, such as a solid cancer selected from the group consisting of lung, prostate, ovarian, brain, breast, skin, bladder, colon, gastrointestinal, head and neck, gastric, pancreas, neurologic, renal, and liver cancer, or a hematological cancer selected from the group consisting of lymphocytic leukemia, myeloid leukemia, non-Hodgkin lymphoma, and Hodgkin lymphoma. In one embodiment, the cancer is colon carcinoma. In one embodiment, the cancer is colon adenocarcinoma. In certain embodiments, the cancer is a BRCA-mutant cancer, such as a BRCA-mutant ovarian cancer and a BRCA-mutant breast cancer.

The combination therapy of the present disclosure may be applied to animals, preferably mammals (e.g., domesticated animals, cats, dogs, mice, rats), and more preferably humans. Any method of administration may be used to deliver the compound of formula I, the PARP inhibitor, and/or the chemotherapeutic agent to the subject in need thereof. In certain embodiments, the compound of formula I, the chemotherapeutic agent, and/or the PARP inhibitor are administered orally. In other embodiments, the compound of formula I, the chemotherapeutic agent, and/or the PARP inhibitor are administered parenterally.

One or more additional pharmaceutical agents or treatment methods such as, for example, immune enhancers, immunosuppressants, anti-tumor vaccines, cytokine therapy (e.g., IL2 and GM-CSF), and/or tyrosine kinase inhibitors can be optionally used in combination with the combination therapy of the disclosure. The additional agents can be combined with the combination therapeutics of the disclosure in a single dosage form, or these agents can be administered simultaneously or sequentially as separate dosage forms.

Pharmaceutical Compositions and Dosing

The disclosure also provides pharmaceutically acceptable compositions which comprise a therapeutically effective amount of one or more compounds of Formula I, formulated together with one or more pharmaceutically acceptable carriers (additives) and/or diluents, a therapeutically effective amount of the PARP inhibitor mentioned above, formulated together with one or more pharmaceutically acceptable carriers (additives) and/or diluents, optionally a therapeutically effective amount of the chemotherapeutic agent mentioned above, formulated together with one or more pharmaceutically acceptable carriers (additives) and/or diluents, and optionally, one or more additional therapeutic agents if needed. The compounds of the disclosure can be administered by any suitable means, for example, orally, as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. The chemotherapeutic agent of the disclosure can be administered by any suitable means with a pharmaceutically acceptable carrier. The PARP inhibitor of the disclosure can be administered by any suitable means with a pharmaceutically acceptable carrier. The pharmaceutical composition of the present disclosure can also be prepared as liposomes and nanoparticles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The dosage regimen for the compounds, the chemotherapeutic agent, and/or the PARP inhibitor of the disclosure will, of course, vary depending upon known factors, such as the pharmacodynamic characteristics of each particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion.

The compound, the immunotherapeutic agent or the cancer-promoting molecule targeting therapeutic agent, and optionally the chemotherapeutic agent, of this disclosure may be administered in a single daily dose, or the total daily dosage may be administered in divided doses of two, three, or four times daily.

EXAMPLES

Example 1. Combination of CHK Inhibitor and PARP Inhibitor Synergistically Induced Tumor Cell Death MCF7F cells (fulvestrant-resistant) were maintained at 37° C. in 5% $CO_2$ in RPMI 1640 medium (10-040-CV, Coming cellgro) supplemented with 10% FBS (10270-106, GIBCO), 1% penicillin and 1% streptomycin, and used before the 10th subculture, wherein these cells were in house prepared by culturing MCF7 cells (TCHu 74, National Collection of Authenticated Cell Cultures) in medium containing 1 μM fulvestrant for approximately 18 months (Hong Liu et al., Cooperative effect of gefitinib and fumitremorgin c on cell growth and chemosensitivity in estrogen receptor alpha negative fulvestrant-resistant MCF-7 cells. *Int J Oncol.* 2006. 29(5):1237-1246).

A CHK1 inhibitor, 2-(3-fluorophenyl)-4-(3-piperidineamino)-thieno[2,3-d]pyridazine-7-carboxylic acid amide (also referred to as Compound 605B herein), was tested for its inhibitory effect on MCF7F cells, alone or with two commercially available PARP inhibitors, i.e., AZD2281 (Olaparib) and ABT888 (Veliparib).

Briefly, the MCF7F cells were cultured at 37° C. in 5% $CO_2$ in RPMI 1640 medium supplemented with i) 10% FBS, ii) 1% penicillin and 1% streptomycin, and iii) AZD2281 (final concentration at 800 nM), ABT888 (final concentration at 800 nM), Compound 605B (final concentration at 25 nM), 605B+AZD2281 (final concentration at 25 nM and 800 nM), 605B+ABT888 (final concentration at 25 nM and 800 nM), or PBS (vehicle), for 48 hours. Then, cell viability was determined by a MTT assay. The test was done in triplicate.

Cell death rate was calculated by the following formula.

$$\text{Cell death rate}=[1-(OD_{test}-OD_{vehicle})]\times 100\%$$

Cell death rates were analyzed using student's t-test, and group differences were deemed statistically significant when the p-value was lower than 0.05. Zheng-Jun Jin's Q value was calculated using the formula $Q=E_{A+B}/(E_A+E_B-E_A\times E_B)$ to assess the combined effect of Compound 605B and the PARP inhibitor, wherein $E_{A+B}$, $E_A$, and $E_B$ referred to the cell death rates caused by the combined treatment, 605B treatment and PARP inhibitor treatment, respectively. A Q value higher than 1.15 meant a synergistic or additive effect.

The cell death rates were shown in Table 1 and FIG. 1.

TABLE 1

Cell death rates in different groups

| Group | Test articles | Final concentration | Cell Death Rate/% 1 | 2 | 3 | mean |
|---|---|---|---|---|---|---|
| 1 | Vehicle | n.a. | 4.69 | 5.13 | 4.05 | 4.62 |
| 2 | AZD2281 | 800 nM | 5.86 | 5.42 | 5.37 | 5.55 |
| 3 | ABT888 | 800 nM | 4.69 | 4.28 | 4.93 | 4.63 |
| 4 | 605B | 25 nM | 5.03 | 5.22 | 4.67 | 4.97 |
| 5 | 605B<br>AZD2281 | 25 nM<br>800 nM | 24.91 | 24.66 | 24.07 | 24.55 |
| 6 | 605B<br>ABT888 | 25 nM<br>800 nM | 23.44 | 23.89 | 23.05 | 23.46 |

It can be seen that Compound 605B and the PARP inhibitor, when used alone, had little inhibitory effects on cells, while their combined use significantly increased the cell death rates.

The Zheng-Jun Jin's Q value for the combined use of 605B and AZD2281 was 2.40, and that for the combined use of 605B and ABT888 was determined to be 2.50, suggesting that Compound 605B worked synergistically with the two PARP inhibitors to induce more tumor cell death.

Example 2. Combination of CHK Inhibitor and PARP Inhibitor AZD2281 Synergistically Induced Tumor Cell Death The combined use of Compound 605 and AZD2281 was further tested in other breast cancer cell lines, including BT474 (TCHu 143, National collection of Authenticated Cell Cultures), MCF7 (TCHu 74, National collection of Authenticated Cell Cultures), and MMTV-HER2 (a gift from Dr. Liguang-L, Shanghai Institute of Materia Medica, Chinese Academy of Sciences).

Briefly, these cells were cultured at 37° C. in 5% $CO_2$ in RPMI 1640 medium supplemented with i) 10% FBS, ii) 1% penicillin and streptomycin, and iii) AZD2281 (final concentration at 800 nM), Compound 605B (final concentration at 25 nM), 605B+AZD2281 (final concentration at 25 nM and 800 nM), or PBS, for 48 hours. Then, cell viability was determined by a MTT assay. The test was done in triplicate.

Figure 2:
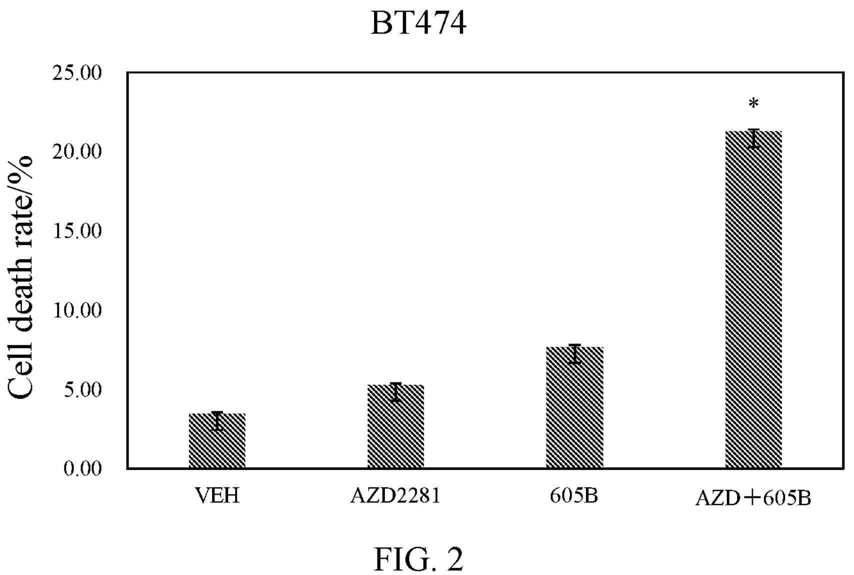
FIG. 2 is a column graph showing the death rates of BT474 cells treated with 605B, AZD2281, and 605B+AZD2281, respectively.
Figure 3:
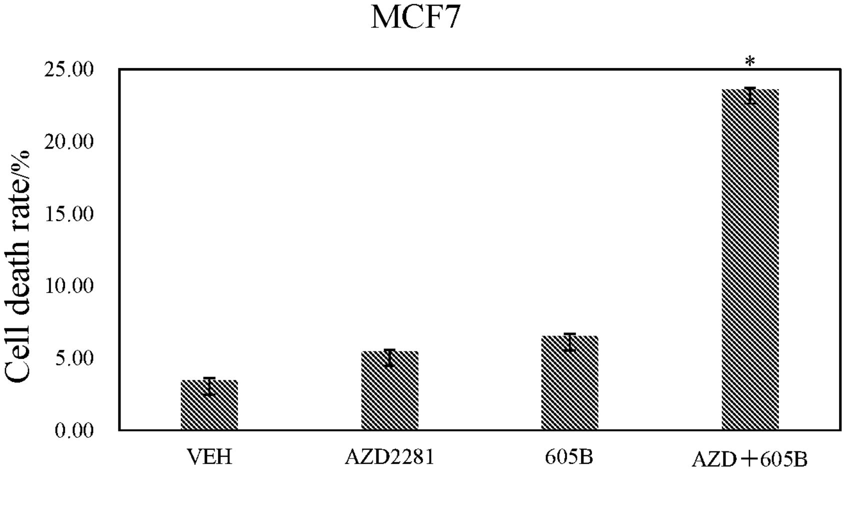
FIG. 3 is a column graph showing the death rates of MCF7 cells treated with 605B, AZD2281, and 605B+AZD2281, respectively.
Figure 4:
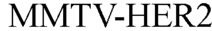
FIG. 4 is a column graph showing the death rates of MMTV-HER2 cells treated with 605B, AZD2281, and 605B+AZD2281, respectively.
Figure 4:
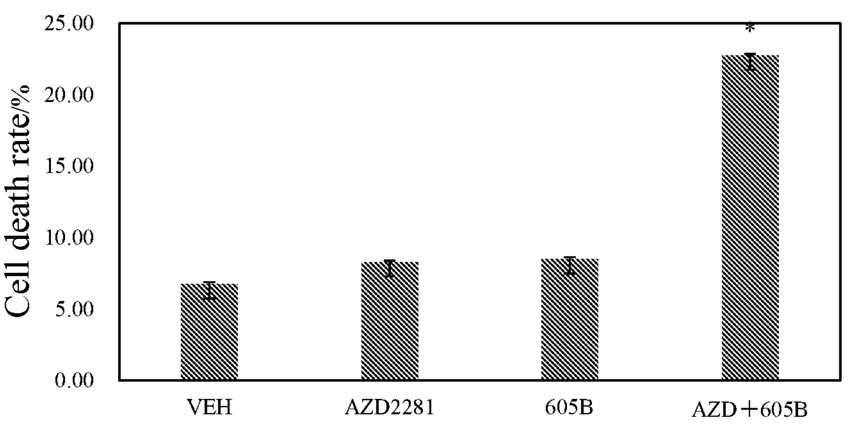

The results were summarized and shown in Table 2 below and FIGS. 2 to 4.

TABLE 2

Cell death rates and Zheng-Jun Jin's Q values

| Cell line | Test articles | Final concentration | Cell Death Rate/% 1 | 2 | 3 | mean | Zheng-Jun Jin's Q value |
|---|---|---|---|---|---|---|---|
| BT474 | Vehicle | n.a. | 3.61 | 3.25 | 3.51 | 3.46 | |
| | AZD2281 | 800 nM | 5.47 | 5.1 | 5.27 | 5.28 | |
| | 605B | 25 nM | 7.72 | 7.45 | 7.83 | 7.67 | |
| | AZD2281 + 605B | 800 nM + 25 nM | 21.37 | 21.69 | 20.84 | 21.30 | 1.70 |
| MCF7 | Vehicle | n.a. | 3.72 | 3.48 | 3.24 | 3.72 | |
| | AZD2281 | 800 nM | 5.34 | 5.39 | 5.66 | 5.34 | |
| | 605B | 25 nM | 6.51 | 6.38 | 6.72 | 6.51 | |
| | AZD2281 + 605B | 800 nM + 25 nM | 23.67 | 23.88 | 23.35 | 23.67 | 2.05 |
| MMTV-HER2 | Vehicle | n.a. | 6.98 | 6.74 | 6.52 | 6.75 | |
| | AZD2281 | 800 nM | 8.34 | 8.46 | 8.05 | 8.28 | |
| | 605B | 25 nM | 8.69 | 8.33 | 8.47 | 8.50 | |
| | AZD2281 + 605B | 800 nM + 25 nM | 22.87 | 22.52 | 22.91 | 22.77 | 1.41 |

The data showed that Compound 605B worked with AZD2281 in a synergic manner to induce breast cancer cell death.

Example 3. Combination of CHK Inhibitor and PARP Inhibitor AG014699 Synergistically Induced Tumor Cell Death Compound 605B was tested with another PARP inhibitor, AG014699 (Rucaparib), for the inhibitory effects on breast tumor cell lines, including BT474, MCF7, and MMTV-HER2.

Briefly, these cells were cultured at 37° C. in 5% $CO_2$ in RPMI 1640 medium supplemented with i) 10% FBS, ii) 1% penicillin and 1% streptomycin, and iii) AZD2281 (final concentration at 800 nM), Compound 605B (final concentration at 25 nM), 605B+AZD2281 (final concentration at 25 nM and 800 nM), or PBS, for 48 hours. Then, cell viability was determined by the MTT assay. The test was done in triplicate.

Figure 5:
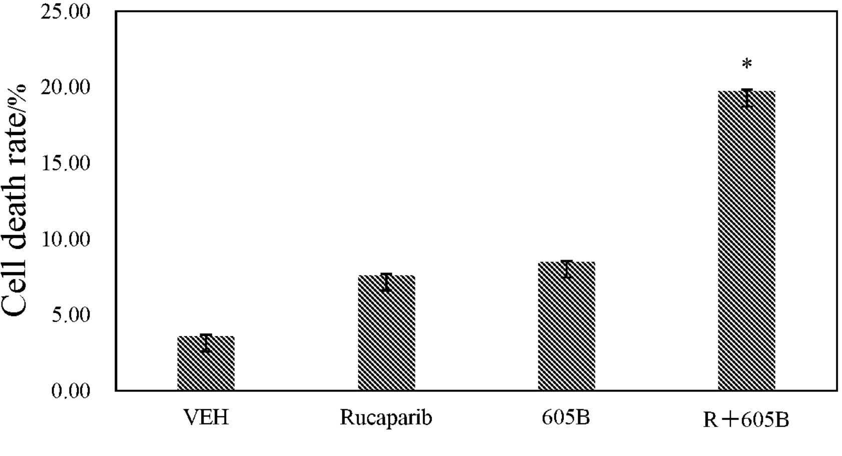
FIG. 5 is a column graph showing the death rates of BT474 cells treated with 605B, Rucaparib, and 605B+Rucaparib, respectively.
Figure 6:
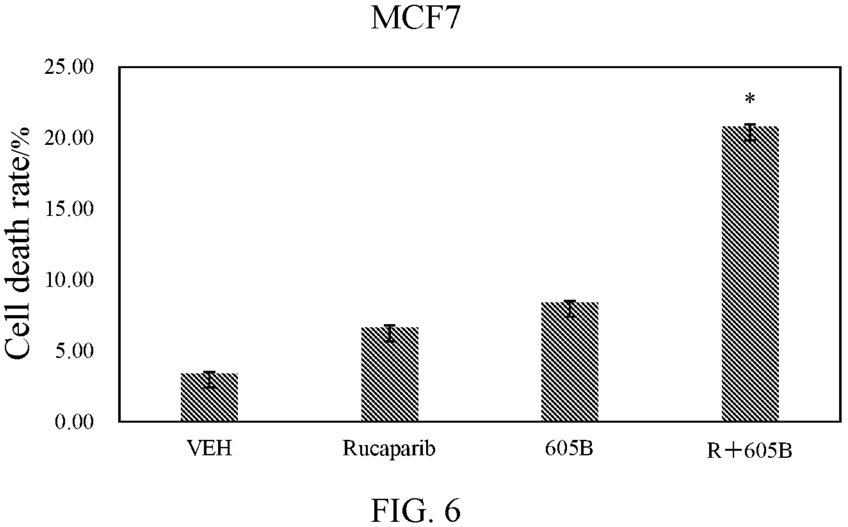
FIG. 6 is a column graph showing the death rates of MCF7 cells treated with 605B, Rucaparib, and 605B+Rucaparib, respectively.
Figure 7:
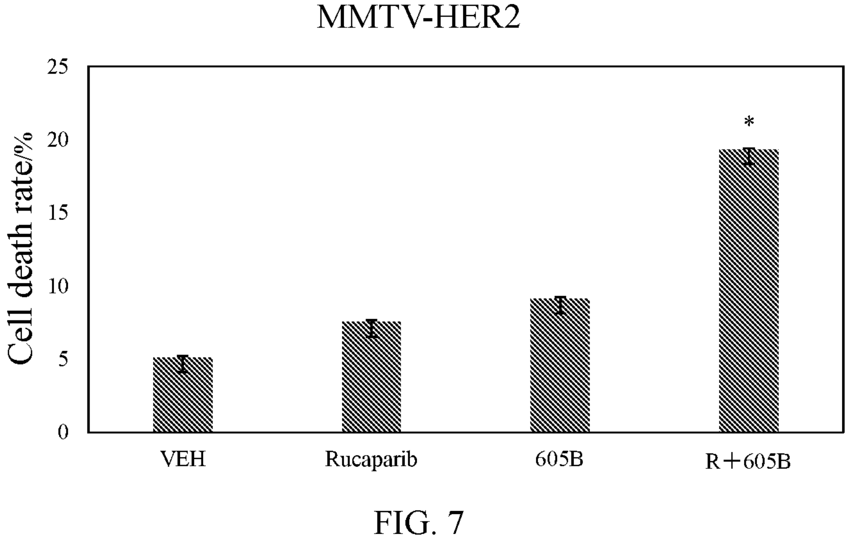
FIG. 7 is a column graph showing the death rates of MMTV-HER2 cells treated with 605B, Rucaparib, and 605B+Rucaparib, respectively.

The results were summarized and shown in Table 3 below and FIGS. 5 to 7.

TABLE 3

Cell death rates and Zheng-Jun Jin's Q values

| Cell line | Test articles | Final concentration | Cell Death Rate/% 1 | 2 | 3 | mean | Zheng-Jun Jin's Q value |
|---|---|---|---|---|---|---|---|
| BT474 | Vehicle | n.a. | 3.75 | 3.61 | 3.45 | 3.60 | |
| | Rucaparib | 800 nM | 7.63 | 7.77 | 7.39 | 7.60 | |
| | 605B | 25 nM | 8.49 | 8.24 | 8.67 | 8.47 | |
| | Rucaparib + 605B | 800 nM + 25 nM | 19.75 | 19.85 | 19.56 | 19.72 | 1.28 |

TABLE 3-continued

Cell death rates and Zheng-Jun Jin's Q values

| Cell line | Test articles | Final concentration | Cell Death Rate/% 1 | 2 | 3 | mean | Zheng-Jun Jin's Q value |
|---|---|---|---|---|---|---|---|
| MCF7 | Vehicle | n.a. | 3.44 | 3.23 | 3.57 | 3.41 | |
| | Rucaparib | 800 nM | 6.88 | 6.46 | 6.65 | 6.66 | |
| | 605B | 25 nM | 8.5 | 8.39 | 8.33 | 8.41 | |
| | Rucaparib + 605B | 800 nM + 25 nM | 20.98 | 20.74 | 20.75 | 20.82 | 1.43 |
| MMTV-HER2 | Vehicle | n.a. | 5.12 | 4.89 | 5.2 | 5.07 | |
| | Rucaparib | 800 nM | 7.54 | 7.68 | 7.29 | 7.50 | |
| | 605B | 25 nM | 9.13 | 8.90 | 9.29 | 9.11 | |
| | Rucaparib + 605B | 800 nM + 25 nM | 19.33 | 19.47 | 19.12 | 19.31 | 1.21 |

The data showed that Compound 605B worked with Rucaparib in a synergic manner to induce breast cancer cell death.

The invention claimed is:

1. A method for treating a cancer selected from breast cancer, colon cancer, ovarian cancer, or pancreatic cancer in a subject in need thereof, comprising administering to a subject in need thereof a therapeutically effective amount of a compound of formula I or a pharmaceutically acceptable salt thereof, in combination with a poly(ADP)-ribose polymerase inhibitor, (I)

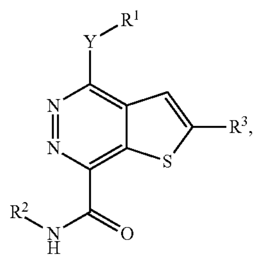

wherein Y is NH, O, S, or $CH_2$;

$R^1$ is selected from the group consisting of:

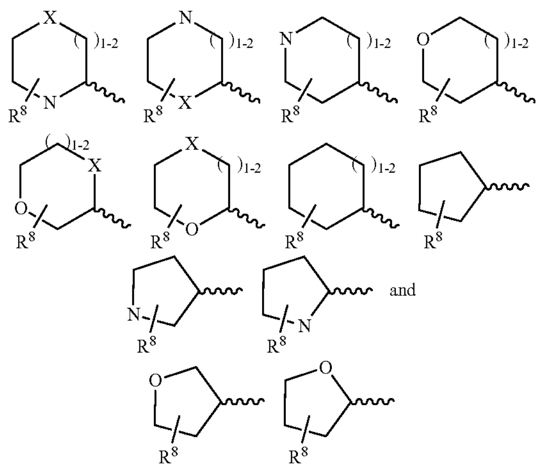

wherein X is $CH_2$, NH, S, or O, $R^8$=—H, —$NH_2$, —OH, or —$N(R^4, R^5)$, wherein $R^4$ and $R^5$, $R^6$are independently H or $C_1$-$C_6$ alkyl, $R^2$ is selected from the group consisting of H, OH, $NH_2$, $OR^{14}$, $NR^{14}R^{15}$, $C_1$-$C_6$ alkyl, $C_2$-$C_8$ alkenyl, and $C_2$-$C_8$ alkynyl, wherein $R^{14}$ and $R^{15}$ are independently H or $C_1$-$C_6$ alkyl, and $R^3$ is selected from the group consisting of:

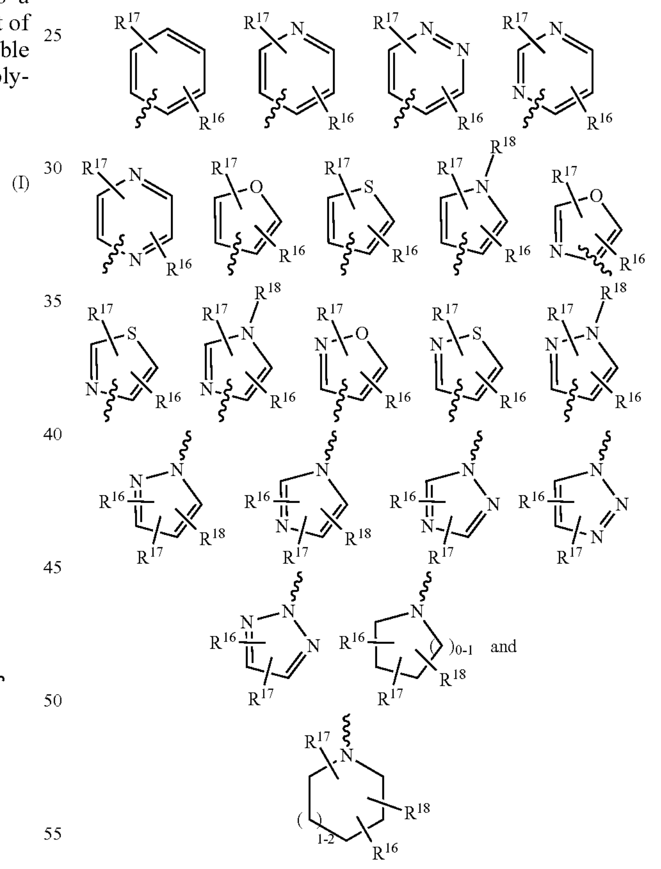

wherein $R^{16}$, $R^{17}$, and $R^{18}$ are independently selected from H, F, Cl, Br, I, and $C_1$-$C_8$ alkyl.

2. The method according to claim 1, wherein Y is NH.

3. The method according to claim 1, wherein Y is O.

4. The method according to claim 1, wherein Y is S.

5. The method according to claim 1, wherein Y is $CH_2$.

6. The method according to claim 1, wherein the poly (ADP)-ribose polymerase inhibitor is Olaparib, Rucaparib, Niraparib, or Talazoparib.

7. The method according to claim 1, wherein the subject is further administered with a chemotherapeutic agent.

8. The method according to claim 7, wherein the chemotherapeutic agent is selected from the group consisting of cisplatin, pemetrexed, gemcitabine, cytarabine, hydroxycarbamide, temozolomide, irinotecan, cyclophosphamide, mitoxantrone, etoposide, folinic acid, fludarabine, and fluorouracil.

9. The method according to claim 1, wherein the cancer is BRCA-mutant.

10. The method according to claim 1, wherein the compound of formula I is selected from the group consisting of 2-(3-fluorophenyl)-4-(3-piperidineamino)-thieno [2,3-d] pyridazine-7-carboxylic acid amide,
2-(3-fluorophenyl)-4-(3-piperidinyloxy)-thieno [2,3-d] pyridazine-7-carboxylic acid amide,
2-(3-fluorophenyl)-4-(3-piperidinylthio)-thieno [2,3-d] pyridazine-7-carboxylic acid amide,
2-(4-chlorophenyl)-4-(3-piperidinyloxy)-thieno [2,3-d] pyridazine-7-carboxylic acid amide,
2-(4-chlorophenyl)-4-(3-piperidinylthio)-thieno [2,3-d] pyridazine-7-carboxylic acid amide,
2-(3,5-dichlorophenyl)-4-(3-piperidinemethyl)-thieno [2,3-d] pyridazinyl-7-formamide,
2-(4-fluorophenyl)-4-(3-piperidineamino)-thieno [2,3-d] pyridazine-7-carboxylic acid amide,
2-(4-chlorophenyl)-4-(3-piperidineamino)-thieno [2,3-d] pyridazine-7-carboxylic acid amide,
2-(4-bromophenyl)-4-(3-piperidineamino)-thieno [2,3-d] pyridazine-7-carboxylic acid amide,
2-(4-fluorophenyl)-4-(3-tetrahydropyran-amino)-thieno [2,3-d] pyridazine-7-carboxylic acid amide,
2-(4-chlorophenyl)-4-(3-tetrahydropyran-amino)-thieno [2,3-d] pyridazine-7-carboxylic acid amide,
2-(4-bromophenyl)-4-(3-tetrahydropyran-amino)-thieno [2,3-d] pyridazine-7-carboxylic acid amide,
2-(4-chlorophenyl)-4-(2-piperidine-amino)-thieno [2,3-d] pyridazine-7-carboxylic acid amide,
2-(4-chlorophenyl)-4-(S-3-piperidine-amino)-thieno [2,3-d] pyridazine-7-carboxylic acid amide,
2-(4-chlorophenyl)-4-(R-3-piperidine-amino)-thieno [2,3-d] pyridazine-7-carboxylic acid amide,
2-(4-chlorophenyl)-4-(3-piperidine-amino)-thieno [2,3-d] pyridazine-7-N-methyl-carboxylic acid amide,
2-(4-chlorophenyl)-4-(3-tetrahydropyran-amino)-thieno [2,3-d] pyridazine-7-N-methyl -carboxylic acid amide,
2-(4-fluorophenyl)-4-(3-tetrahydropyrrol-amino)-thieno [2,3-d] pyridazine-7-carboxylic acid amide,
2-(4-chlorophenyl)-4-(3-tetrahydropyrrol-amino)-thieno [2,3-d] pyridazine-7-carboxylic acid amide,
2-(4-bromophenyl)-4-(3-tetrahydropyrrol-amino)-thieno [2,3-d] pyridazine-7-carboxylic acid amide,
2-(4-fluorophenyl)-4-(3-tetrahydrofuran-amino)-thieno [2,3-d] pyridazine-7-carboxylic acid amide,
2-(4-chlorophenyl)-4-(3-tetrahydrofuran-amino)-thieno [2,3-d] pyridazine-7-carboxylic acid amide,
2-(4-bromophenyl)-4-(3-tetrahydrofuran-amino)-thieno [2,3-d] pyridazine-7-carboxylic acid amide,
2-(4-fluorophenyl)-4-(3-tetrahydrothieno-amino)-thieno [2,3-d] pyridazine-7-carboxylic acid amide,
2-(4-chlorophenyl)-4-(3-tetrahydrothieno-amino)-thieno [2,3-d] pyridazine-7-carboxylic acid amide,
2-(4-bromophenyl)-4-(3-tetrahydrothieno-amino)-thieno [2,3-d] pyridazine-7-carboxylic acid amide,
2-(4-chlorophenyl)-4-(2-tetrahydropyrrol-amino)-thieno [2,3-d] pyridazine-7-carboxylic acid amide,
2-(4-chlorophenyl)-4-(S-3-tetrahydropyrrol-amino)-thieno [2,3-d] pyridazine-7-carboxylic acid amide,
2-(4-chlorophenyl)-4-(R-3-tetrahydropyrrol-amino)-thieno [2,3-d] pyridazine-7-carboxylic acid amide,
2-(4-chlorophenyl)-4-(3-tetrahydropyrrol-amino)-thieno [2,3-d] pyridazine-7-N-methyl -carboxylic acid amide,
2-(4-chlorophenyl)-4-(3-tetrahydrothieno-amino)-thieno [2,3-d] pyridazine-7-N-methyl -carboxylic acid amide,
2-(4-chlorophenyl)-4-(3-tetrahydrofuran-amino)-thieno [2,3-d] pyridazine-7-N-methyl -carboxylic acid amide,
2-(4-fluorophenyl)-4-(3-pyridin-amino)-thieno [2,3-d] pyridazine-7-carboxylic acid amide,
2-(4-chlorophenyl)-4-(3-pyridin-amino)-thieno [2,3-d] pyridazine-7-carboxylic acid amide,
2-(4-bromophenyl)-4-(3-pyridin-amino)-thieno [2,3-d] pyridazine-7-carboxylic acid amide,
2-(4-fluorophenyl)-4-(3-α-pyran-amino)-thieno [2,3-d] pyridazine-7-carboxylic acid amide,
2-(4-chlorophenyl)-4-(3-α-pyran-amino)-thieno [2,3-d] pyridazine-7-carboxylic acid amide,
2-(4-bromophenyl)-4-(3-α-pyran-amino)-thieno [2,3-d] pyridazine-7-carboxylic acid amide,
2-(4-chlorophenyl)-4-(2-pyridin-amino)-thieno [2,3-d] pyridazine-7-carboxylic acid amide,
2-(4-chlorophenyl)-4-(4-pyridin-amino)-thieno [2,3-d] pyridazine-7-carboxylic acid amide,
2-(4-chlorophenyl)-4-(S-3-pyridin-amino)-thieno [2,3-d] pyridazine-7-carboxylic acid amide,
2-(4-chlorophenyl)-4-(R-3-pyridin-amino)-thieno [2,3-d] pyridazine-7-carboxylic acid amide,
2-(4-chlorophenyl)-4-(3-pyridin-amino)-thieno [2,3-d] pyridazine-7-N-methyl-carboxylic acid amide,
2-(4-chlorophenyl)-4-(3-pyran-amino)-thieno [2,3-d] pyridazine-7-N-methyl-carboxylic acid amide,
2-(4-fluorophenyl)-4-(3-pyrrol-amino)-thieno [2,3-d] pyridazine-7-carboxylic acid amide,
2-(4-chlorophenyl)-4-(3-pyrrol-amino)-thieno [2,3-d] pyridazine-7-carboxylic acid amide,
2-(4-bromophenyl)-4-(3-pyrrol-amino)-thieno [2,3-d] pyridazine-7-carboxylic acid amide,
2-(4-fluorophenyl)-4-(3-furan-amino)-thieno [2,3-d] pyridazine-7-carboxylic acid amide,
2-(4-chlorophenyl)-4-(3-furan-amino)-thieno [2,3-d] pyridazine-7-carboxylic acid amide,
2-(4-bromophenyl)-4-(3-furan-amino)-thieno [2,3-d] pyridazine-7-carboxylic acid amide,
2-(4-fluorophenyl)-4-(3-thieno-amino)-thieno [2,3-d] pyridazine-7-carboxylic acid amide,
2-(4-chlorophenyl)-4-(3-thieno-amino)-thieno [2,3-d] pyridazine-7-carboxylic acid amide,
2-(4-bromophenyl)-4-(3-thieno-amino)-thieno [2,3-d] pyridazine-7-carboxylic acid amide,
2-(4-chlorophenyl)-4-(2-pyrrol-amino)-thieno [2,3-d] pyridazine-7-carboxylic acid amide,
2-(4-chlorophenyl)-4-(S-3-pyrrol-amino)-thieno [2,3-d] pyridazine-7-carboxylic acid amide,
2-(4-chlorophenyl)-4-(R-3-pyrrol-amino)-thieno [2,3-d] pyridazine-7-carboxylic acid amide,
2-(4-chlorophenyl)-4-(3-pyrrol-amino)-thieno [2,3-d] pyridazine-7-N-methyl-carboxylic acid amide,
2-(4-chlorophenyl)-4-(3-thieno-amino)-thieno [2,3-d] pyridazine-7-N-methyl-carboxylic acid amide,
2-(4-chlorophenyl)-4-(3-furan-amino)-thieno [2,3-d] pyridazine-7-N-methyl-carboxylic acid amide,
2-(3-chlorophenyl)-4-(3-piperidineamino)-thieno [2,3-d] pyridazine-7-carboxylic acid amide, 2-(3-bromophenyl)-4-(3-piperidineamino)-thieno [2,3-d] pyridazine-7-carboxylic acid amide,
2-(3-chlorophenyl)-4-(3-tetrahydropyran-amino)-thieno [2,3-d] pyridazine-7-N-methyl -carboxylic acid amide,
2-(3-fluorophenyl)-4-(3-tetrahydropyrrol-amino)-thieno [2,3-d] pyridazine-7-carboxylic acid amide,
2-(3-chlorophenyl)-4-(3-tetrahydropyrrol-amino)-thieno [2,3-d] pyridazine-7-carboxylic acid amide,
2-(3-bromophenyl)-4-(3-tetrahydropyrrol-amino)-thieno [2,3-d] pyridazine-7-carboxylic acid amide,
2-(3-fluorophenyl)-4-(3-tetrahydrofuran-amino)-thieno [2,3-d] pyridazine-7-carboxylic acid amide,
2-(3-chlorophenyl)-4-(3-tetrahydrofuran-amino)-thieno [2,3-d] pyridazine-7-carboxylic acid amide,
2-(3-bromophenyl)-4-(3-tetrahydrofuran-amino)-thieno [2,3-d] pyridazine-7-carboxylic acid amide,
2-(3-fluorophenyl)-4-(3-tetrahydrothieno-amino)-thieno [2,3-d] pyridazine-7-carboxylic acid amide,
2-(3-chlorophenyl)-4-(3-tetrahydrothieno-amino)-thieno [2,3-d] pyridazine-7-carboxylic acid amide,
2-(3-bromophenyl)-4-(3-tetrahydrothieno-amino)-thieno [2,3-d] pyridazine-7-carboxylic acid amide,
2-(3-chlorophenyl)-4-(2-tetrahydropyrrol-amino)-thieno [2,3-d] pyridazine-7-carboxylic acid amide,
2-(3-chlorophenyl)-4-(S-3-tetrahydropyrrol-amino)-thieno [2,3-d] pyridazine-7-carboxylic acid amide,
2-(3-chlorophenyl)-4-(R-3-tetrahydropyrrol-amino)-thieno [2,3-d] pyridazine-7-carboxylic acid amide,
2-(3-chlorophenyl)-4-(3-tetrahydropyrrol-amino)-thieno [2,3-d] pyridazine-7-N-methyl -carboxylic acid amide,
2-(3-fluorophenyl)-4-(3-pyridin-amino)-thieno [2,3-d] pyridazine-7-carboxylic acid amide,
2-(3-chlorophenyl)-4-(3-pyridin-amino)-thieno [2,3-d] pyridazine-7-carboxylic acid amide,
2-(3-bromophenyl)-4-(3-pyridin-amino)-thieno [2,3-d] pyridazine-7-carboxylic acid amide,
2-(3-fluorophenyl)-4-(3-α-pyran-amino)-thieno [2,3-d] pyridazine-7-carboxylic acid amide,
2-(3-chlorophenyl)-4-(3-α-pyran-amino)-thieno [2,3-d] pyridazine-7-carboxylic acid amide,
2-(3-bromophenyl)-4-(3-α-pyran-amino)-thieno [2,3-d] pyridazine-7-carboxylic acid amide,
2-(3-chlorophenyl)-4-(2-pyridin-amino)-thieno [2,3-d] pyridazine-7-carboxylic acid amide,
2-(3-chlorophenyl)-4-(4-pyridin-amino)-thieno [2,3-d] pyridazine-7-carboxylic acid amide,
2-(3-chlorophenyl)-4-(S-3-pyridin-amino)-thieno [2,3-d] pyridazine-7-carboxylic acid amide,
2-(3-chlorophenyl)-4-(R-3-pyridin-amino)-thieno [2,3-d] pyridazine-7-carboxylic acid amide,
2-(3-chlorophenyl)-4-(3-pyridin-amino)-thieno [2,3-d] pyridazine-7-N-methyl-carboxylic acid amide,
2-(3-chlorophenyl)-4-(3-pyran-amino)-thieno [2,3-d] pyridazine-7-N-methyl-carboxylic acid amide,
2-(3-fluorophenyl)-4-(3-pyrrol-amino)-thieno [2,3-d] pyridazine-7-carboxylic acid amide,
2-(3-chlorophenyl)-4-(3-pyrrol-amino)-thieno [2,3-d] pyridazine-7-carboxylic acid amide,
2-(3-bromophenyl)-4-(3-pyrrol-amino)-thieno [2,3-d] pyridazine-7-carboxylic acid amide,
2-(3-fluorophenyl)-4-(3-furan-amino)-thieno [2,3-d] pyridazine-7-carboxylic acid amide,
2-(3-chlorophenyl)-4-(3-furan-amino)-thieno [2,3-d] pyridazine-7-carboxylic acid amide,
2-(3-bromophenyl)-4-(3-furan-amino)-thieno [2,3-d] pyridazine-7-carboxylic acid amide,
2-(3-fluorophenyl)-4-(3-thieno-amino)-thieno [2,3-d] pyridazine-7-carboxylic acid amide,
2-(3-chlorophenyl)-4-(3-thieno-amino)-thieno [2,3-d] pyridazine-7-carboxylic acid amide,
2-(3-bromophenyl)-4-(3-thieno-amino)-thieno [2,3-d] pyridazine-7-carboxylic acid amide,
2-(3-chlorophenyl)-4-(2-pyrrol-amino)-thieno [2,3-d] pyridazine-7-carboxylic acid amide,
2-(3-chlorophenyl)-4-(S-3-pyrrol-amino)-thieno [2,3-d] pyridazine-7-carboxylic acid amide,
2-(3-chlorophenyl)-4-(R-3-pyrrol-amino)-thieno [2,3-d] pyridazine-7-carboxylic acid amide,
2-(3-chlorophenyl)-4-(3-pyrrol-amino)-thieno [2,3-d] pyridazine-7-N-methyl-carboxylic acid amide,
2-(3-chlorophenyl)-4-(3-thieno-amino)-thieno [2,3-d] pyridazine-7-N-methyl-carboxylic acid amide,
2-(3-chlorophenyl)-4-(3-furan-amino)-thieno [2,3-d] pyridazine-7-N-methyl-carboxylic acid amide,
2-(4-fluorophenyl)-4-(3-piperidinemethyl)-thieno [2,3-d] pyridazinyl-7-formamide,
2-(4-chlorophenyl)-4-(3-piperidinemethyl)-thieno [2,3-d] pyridazinyl-7-formamide,
2-(4-bromophenyl)-4-(3-piperidinemethyl)-thieno [2,3-d] pyridazinyl-7-formamide,
2-(4-fluorophenyl)-4-(3-tetrahydropyranmethyl)-thieno [2,3-d] pyridazinyl-7-formamide,
2-(4-chlorophenyl)-4-(3-tetrahydropyranmethyl)-thieno [2,3-d] pyridazinyl-7-formamide,
2-(4-bromophenyl)-4-(3-tetrahydropyranmethyl)-thieno [2,3-d] pyridazinyl-7-formamide,
2-(4-chlorophenyl)-4-(2-piperidinemethyl)-thieno [2,3-d] pyridazinyl-7-formamide,
2-(4-chlorophenyl)-4-(4-piperidinemethyl)-thieno [2,3-d] pyridazinyl-7-formamide,
2-(4-chlorophenyl)-4-(S-3-piperidinemethyl)-thieno [2,3-d] pyridazinyl-7-formamide,
2-(4-chlorophenyl)-4-(R-3-piperidinemethyl)-thieno [2,3-d] pyridazinyl-7-formamide,
2-(4-chlorophenyl)-4-(3-piperidinemethyl)-thieno [2,3-d] pyridazinyl-7-N-methyl -formamide,
2-(4-chlorophenyl)-4-(3-tetrahydropyranmethyl)-thieno [2,3-d] pyridazinyl-7-N-methyl-formamide,
2-(4-fluorophenyl)-4-(3-pyrrolidinemethyl)-thieno [2,3-d] pyridazinyl-7-formamide,
2-(4-chlorophenyl)-4-(3-pyrrolidinemethyl)-thieno [2,3-d] pyridazinyl-7-formamide,
2-(4-bromophenyl)-4-(3-pyrrolidinemethyl)-thieno [2,3-d] pyridazinyl-7-formamide,
2-(4-fluorophenyl)-4-(3-tetrahydrofuranmethyl)-thieno [2,3-d] pyridazinyl-7-formamide,
2-(4-chlorophenyl)-4-(3-tetrahydrofuranmethyl)-thieno [2,3-d] pyridazinyl-7-formamide,
2-(4-bromophenyl)-4-(3-tetrahydrofuranmethyl)-thieno [2,3-d] pyridazinyl-7-formamide,
2-(4-fluorophenyl)-4-(3-tetrahydrothiophenemethyl)-thieno [2,3-d] pyridazinyl-7-formamide,
2-(4-chlorophenyl)-4-(3-tetrahydrothiophenemethyl)-thieno [2,3-d] pyridazinyl-7-formamide,
2-(4-bromophenyl)-4-(3-tetrahydrothiophenemethyl)-thieno [2,3-d] pyridazinyl-7-formamide,
2-(4-chlorophenyl)-4-(S-3-pyrrolidinemethyl)-thieno [2,3-d] pyridazinyl-7-formamide,
2-(4-chlorophenyl)-4-(R-3-pyrrolidinemethyl)-thieno [2,3-d] pyridazinyl-7-formamide,
2-(4-chlorophenyl)-4-(3-pyrrolidinemethyl)-thieno [2,3-d] pyridazinyl-7-N-methyl-formamide, 2-(4-chlorophenyl)-4-(3-tetrahydrothiophenemethyl)-thieno [2,3-d] pyridazinyl-7-N-methyl-formamide,
2-(4-chlorophenyl)-4-(3-tetrahydrofuranmethyl)-thieno [2,3-d] pyridazinyl-7-N-methyl-formamide,
2-(4-fluorophenyl)-4-(3-pyridinemethyl)-thieno [2,3-d] pyridazinyl-7-formamide,
2-(4-chlorophenyl)-4-(3-pyridinemethyl)-thieno [2,3-d] pyridazinyl-7-formamide,
2-(4-bromophenyl)-4-(3-pyridinemethyl)-thieno [2,3-d] pyridazinyl-7-formamide,
2-(4-fluorophenyl)-4-(3-α-pyranmethyl)-thieno [2,3-d] pyridazinyl-7-formamide,
2-(4-chlorophenyl)-4-(3-α-pyranmethyl)-thieno [2,3-d] pyridazinyl-7-formamide,
2-(4-bromophenyl)-4-(3-α-pyranmethyl)-thieno [2,3-d] pyridazinyl-7-formamide,
2-(4-fluorophenyl)-4-(3-α-thiopyranmethyl)-thieno [2,3-d] pyridazinyl-7-formamide,
2-(4-chlorophenyl)-4-(3-α-thiopyranmethyl)-thieno [2,3-d] pyridazinyl-7-formamide,
2-(4-bromophenyl)-4-(3-α-thiopyranmethyl)-thieno [2,3-d] pyridazinyl-7-formamide,
2-(4-chlorophenyl)-4-(2-pyridinemethyl)-thieno [2,3-d] pyridazinyl-7-formamide,
2-(4-chlorophenyl)-4-(4-pyridinemethyl)-thieno [2,3-d] pyridazinyl-7-formamide,
2-(4-chlorophenyl)-4-(3-pyridinemethyl)-thieno [2,3-d] pyridazinyl-7-N-methyl formamide,
2-(4-chlorophenyl)-4-(3-thiopyranylmethyl)-thieno [2,3-d] pyridazinyl-7-N-methyl formamide,
2-(4-chlorophenyl)-4-(3-pyranmethyl)-thieno [2,3-d] pyridazinyl-7-N-methyl formamide,
2-(4-fluorophenyl)-4-(3-pyrrolemethyl)-thieno [2,3-d] pyridazinyl-7-formamide,
2-(4-chlorophenyl)-4-(3-pyrrolemethyl)-thieno [2,3-d] pyridazinyl-7-formamide,
2-(4-bromophenyl)-4-(3-pyrrolemethyl)-thieno [2,3-d] pyridazinyl-7-formamide,
2-(4-fluorophenyl)-4-(3-furanmethyl)-thieno [2,3-d] pyridazinyl-7-formamide,
2-(4-chlorophenyl)-4-(3-furanmethyl)-thieno [2,3-d] pyridazinyl-7-formamide,
2-(4-bromophenyl)-4-(3-furanmethyl)-thieno [2,3-d] pyridazinyl-7-formamide,
2-(4-fluorophenyl)-4-(3-thiaphenemethyl)-thieno [2,3-d] pyridazinyl-7-formamide,
2-(4-chlorophenyl)-4-(3-thiaphenemethyl)-thieno [2,3-d] pyridazinyl-7-formamide,
2-(4-bromophenyl)-4-(3-thiaphenemethyl)-thieno [2,3-d] pyridazinyl-7-formamide,
2-(4-chlorophenyl)-4-(2-pyrrolemethyl)-thieno [2,3-d] pyridazinyl-7-formamide,
2-(4-chlorophenyl)-4-(3-pyrrolemethyl)-thieno [2,3-d] pyridazinyl-7-N-methyl formamide,
2-(4-chlorophenyl)-4-(3-thiaphenemethyl)-thieno [2,3-d] pyridazinyl-7-N-methyl formamide, and
2-(4-chlorophenyl)-4-(3-furanmethyl)-thieno [2,3-d] pyridazinyl-7-N-methyl formamide.

11. The method according to claim 10, wherein the cancer is BRCA-mutant.

12. A pharmaceutically acceptable composition, comprising a therapeutically effective amount of a compound of formula I, and a poly (ADP)-ribose polymerase inhibitor, (I)

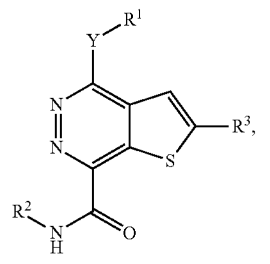

wherein Y is NH, O, S, or $CH_2$;

$R^1$ is selected from the group consisting of:

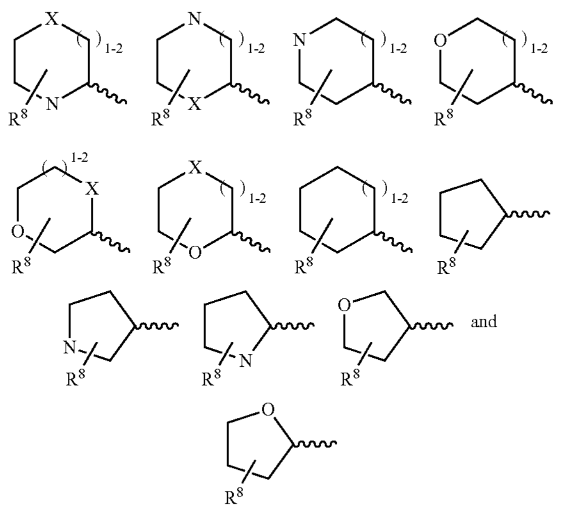

wherein X is $CH_2$, NH, S, or O, $R^8$=—H, —$NH_2$, —OH, or —N($R^4$, $R^5$), wherein $R^4$ and $R^5$ are independently H or $C_1$-$C_6$ alkyl, $R^2$ is selected from the group consisting of H, OH, $NH_2$, $OR^{14}$, $NR^{14}R^{15}$, C1-C6 alkyl, $C_2$-$C_8$ alkenyl, and $C_2$-$C_8$ alkynyl, wherein $R^{14}$ and $R^{15}$ are independently H or $C_1$-$C_6$ alkyl, and $R^3$ is selected from the group consisting of:

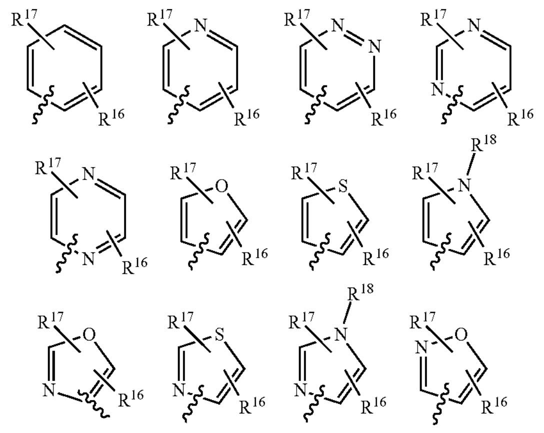

-continued

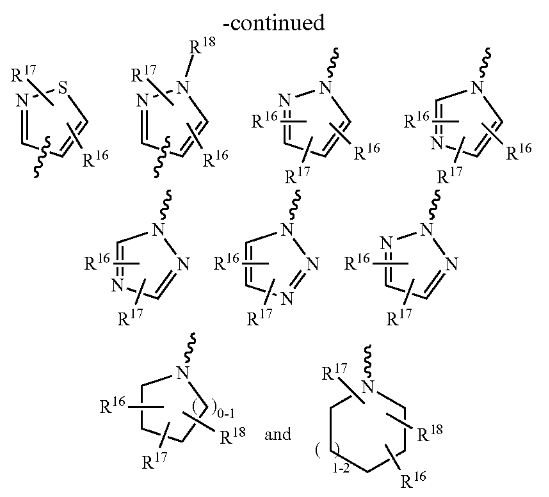

and wherein $R^{16}$, $R^{17}$, and $R^{18}$ are independently selected from H, F, Cl, Br, I, and $C_1$-$C_8$ alkyl.

13. The pharmaceutically acceptable composition of claim 12, wherein the poly(ADP)-ribose polymerase inhibitor is Olaparib, Rucaparib, Niraparib, or Talazoparib.

14. The pharmaceutically acceptable composition according to claim 12, further comprising a chemotherapeutic agent.

15. The pharmaceutically acceptable composition according to claim 12, wherein the compound of formula I is selected from the group consisting of 2-(3-fluorophenyl)-4-(3-piperidineamino)-thieno [2,3-d] pyridazine-7-carboxylic acid amide,
2-(3-fluorophenyl)-4-(3-piperidinyloxy)-thieno [2,3-d] pyridazine-7-carboxylic acid amide,
2-(3-fluorophenyl)-4-(3-piperidinylthio)-thieno [2,3-d] pyridazine-7-carboxylic acid amide,
2-(4-chlorophenyl)-4-(3-piperidinyloxy)-thieno [2,3-d] pyridazine-7-carboxylic acid amide,
2-(4-chlorophenyl)-4-(3-piperidinylthio)-thieno [2,3-d] pyridazine-7-carboxylic acid amide,
2-(3,5-dichlorophenyl)-4-(3-piperidinemethyl)-thieno [2,3-d] pyridazinyl-7-formamide,
2-(4-fluorophenyl)-4-(3-piperidineamino)-thieno [2,3-d] pyridazine-7-carboxylic acid amide,
2-(4-chlorophenyl)-4-(3-piperidineamino)-thieno [2,3-d] pyridazine-7-carboxylic acid amide,
2-(4-bromophenyl)-4-(3-piperidineamino)-thieno [2,3-d] pyridazine-7-carboxylic acid amide,
2-(4-fluorophenyl)-4-(3-tetrahydropyran-amino)-thieno [2,3-d] pyridazine-7-carboxylic acid amide,
2-(4-chlorophenyl)-4-(3-tetrahydropyran-amino)-thieno [2,3-d] pyridazine-7-carboxylic acid amide,
2-(4-bromophenyl)-4-(3-tetrahydropyran-amino)-thieno [2,3-d] pyridazine-7-carboxylic acid amide,
2-(4-chlorophenyl)-4-(2-piperidine-amino)-thieno [2,3-d] pyridazine-7-carboxylic acid amide,
2-(4-chlorophenyl)-4-(S-3-piperidine-amino)-thieno [2,3-d] pyridazine-7-carboxylic acid amide,
2-(4-chlorophenyl)-4-(R-3-piperidine-amino)-thieno [2,3-d] pyridazine-7-carboxylic acid amide,
2-(4-chlorophenyl)-4-(3-piperidine-amino)-thieno [2,3-d] pyridazine-7-N-methyl-carboxylic acid amide,
2-(4-chlorophenyl)-4-(3-tetrahydropyran-amino)-thieno [2,3-d] pyridazine-7-N-methyl -carboxylic acid amide,
2-(4-fluorophenyl)-4-(3-tetrahydropyrrol-amino)-thieno [2,3-d] pyridazine-7-carboxylic acid amide,
2-(4-chlorophenyl)-4-(3-tetrahydropyrrol-amino)-thieno [2,3-d] pyridazine-7-carboxylic acid amide,
2-(4-bromophenyl)-4-(3-tetrahydropyrrol-amino)-thieno [2,3-d] pyridazine-7-carboxylic acid amide,
2-(4-fluorophenyl)-4-(3-tetrahydrofuran-amino)-thieno [2,3-d] pyridazine-7-carboxylic acid amide,
2-(4-chlorophenyl)-4-(3-tetrahydrofuran-amino)-thieno [2,3-d] pyridazine-7-carboxylic acid amide,
2-(4-bromophenyl)-4-(3-tetrahydrofuran-amino)-thieno [2,3-d] pyridazine-7-carboxylic acid amide,
2-(4-fluorophenyl)-4-(3-tetrahydrothieno-amino)-thieno [2,3-d] pyridazine-7-carboxylic acid amide,
2-(4-chlorophenyl)-4-(3-tetrahydrothieno-amino)-thieno [2,3-d] pyridazine-7-carboxylic acid amide,
2-(4-bromophenyl)-4-(3-tetrahydrothieno-amino)-thieno [2,3-d] pyridazine-7-carboxylic acid amide,
2-(4-chlorophenyl)-4-(2-tetrahydropyrrol-amino)-thieno [2,3-d] pyridazine-7-carboxylic acid amide,
2-(4-chlorophenyl)-4-(S-3-tetrahydropyrrol-amino)-thieno [2,3-d] pyridazine-7-carboxylic acid amide,
2-(4-chlorophenyl)-4-(R-3-tetrahydropyrrol-amino)-thieno [2,3-d] pyridazine-7-carboxylic acid amide,
2-(4-chlorophenyl)-4-(3-tetrahydropyrrol-amino)-thieno [2,3-d] pyridazine-7-N-methyl -carboxylic acid amide,
2-(4-chlorophenyl)-4-(3-tetrahydrothieno-amino)-thieno [2,3-d] pyridazine-7-N-methyl -carboxylic acid amide,
2-(4-chlorophenyl)-4-(3-tetrahydrofuran-amino)-thieno [2,3-d] pyridazine-7-N-methyl -carboxylic acid amide,
2-(4-fluorophenyl)-4-(3-pyridin-amino)-thieno [2,3-d] pyridazine-7-carboxylic acid amide,
2-(4-chlorophenyl)-4-(3-pyridin-amino)-thieno [2,3-d] pyridazine-7-carboxylic acid amide,
2-(4-bromophenyl)-4-(3-pyridin-amino)-thieno [2,3-d] pyridazine-7-carboxylic acid amide,
2-(4-fluorophenyl)-4-(3-α-pyran-amino)-thieno [2,3-d] pyridazine-7-carboxylic acid amide,
2-(4-chlorophenyl)-4-(3-α-pyran-amino)-thieno [2,3-d] pyridazine-7-carboxylic acid amide,
2-(4-bromophenyl)-4-(3-α-pyran-amino)-thieno [2,3-d] pyridazine-7-carboxylic acid amide,
2-(4-chlorophenyl)-4-(2-pyridin-amino)-thieno [2,3-d] pyridazine-7-carboxylic acid amide,
2-(4-chlorophenyl)-4-(4-pyridin-amino)-thieno [2,3-d] pyridazine-7-carboxylic acid amide,
2-(4-chlorophenyl)-4-(S-3-pyridin-amino)-thieno [2,3-d] pyridazine-7-carboxylic acid amide,
2-(4-chlorophenyl)-4-(R-3-pyridin-amino)-thieno [2,3-d] pyridazine-7-carboxylic acid amide,
2-(4-chlorophenyl)-4-(3-pyridin-amino)-thieno [2,3-d] pyridazine-7-N-methyl-carboxylic acid amide,
2-(4-chlorophenyl)-4-(3-pyran-amino)-thieno [2,3-d] pyridazine-7-N-methyl-carboxylic acid amide,
2-(4-fluorophenyl)-4-(3-pyrrol-amino)-thieno [2,3-d] pyridazine-7-carboxylic acid amide,
2-(4-chlorophenyl)-4-(3-pyrrol-amino)-thieno [2,3-d] pyridazine-7-carboxylic acid amide,
2-(4-bromophenyl)-4-(3-pyrrol-amino)-thieno [2,3-d] pyridazine-7-carboxylic acid amide,
2-(4-fluorophenyl)-4-(3-furan-amino)-thieno [2,3-d] pyridazine-7-carboxylic acid amide,
2-(4-chlorophenyl)-4-(3-furan-amino)-thieno [2,3-d] pyridazine-7-carboxylic acid amide,
2-(4-bromophenyl)-4-(3-furan-amino)-thieno [2,3-d] pyridazine-7-carboxylic acid amide,
2-(4-fluorophenyl)-4-(3-thieno-amino)-thieno [2,3-d] pyridazine-7-carboxylic acid amide, 2-(4-chlorophenyl)-4-(3-thieno-amino)-thieno [2,3-d] pyridazine-7-carboxylic acid amide, 2-(4-bromophenyl)-4-(3-thieno-amino)-thieno [2,3-d] pyridazine-7-carboxylic acid amide, 2-(4-chlorophenyl)-4-(2-pyrrol-amino)-thieno [2,3-d] pyridazine-7-carboxylic acid amide, 2-(4-chlorophenyl)-4-(S-3-pyrrol-amino)-thieno [2,3-d] pyridazine-7-carboxylic acid amide, 2-(4-chlorophenyl)-4-(R-3-pyrrol-amino)-thieno [2,3-d] pyridazine-7-carboxylic acid amide, 2-(4-chlorophenyl)-4-(3-pyrrol-amino)-thieno [2,3-d] pyridazine-7-N-methyl-carboxylic acid amide, 2-(4-chlorophenyl)-4-(3-thieno-amino)-thieno [2,3-d] pyridazine-7-N-methyl-carboxylic acid amide, 2-(4-chlorophenyl)-4-(3-furan-amino)-thieno [2,3-d] pyridazine-7-N-methyl-carboxylic acid amide, 2-(3-chlorophenyl)-4-(3-piperidineamino)-thieno [2,3-d] pyridazine-7-carboxylic acid amide, 2-(3-bromophenyl)-4-(3-piperidineamino)-thieno [2,3-d] pyridazine-7-carboxylic acid amide, 2-(3-chlorophenyl)-4-(3-tetrahydropyran-amino)-thieno [2,3-d] pyridazine-7-N-methyl -carboxylic acid amide, 2-(3-fluorophenyl)-4-(3-tetrahydropyrrol-amino)-thieno [2,3-d] pyridazine-7-carboxylic acid amide, 2-(3-chlorophenyl)-4-(3-tetrahydropyrrol-amino)-thieno [2,3-d] pyridazine-7-carboxylic acid amide, 2-(3-bromophenyl)-4-(3-tetrahydropyrrol-amino)-thieno [2,3-d] pyridazine-7-carboxylic acid amide, 2-(3-fluorophenyl)-4-(3-tetrahydrofuran-amino)-thieno [2,3-d] pyridazine-7-carboxylic acid amide, 2-(3-chlorophenyl)-4-(3-tetrahydrofuran-amino)-thieno [2,3-d] pyridazine-7-carboxylic acid amide, 2-(3-bromophenyl)-4-(3-tetrahydrofuran-amino)-thieno [2,3-d] pyridazine-7-carboxylic acid amide, 2-(3-fluorophenyl)-4-(3-tetrahydrothieno-amino)-thieno [2,3-d] pyridazine-7-carboxylic acid amide, 2-(3-chlorophenyl)-4-(3-tetrahydrothieno-amino)-thieno [2,3-d] pyridazine-7-carboxylic acid amide, 2-(3-bromophenyl)-4-(3-tetrahydrothieno-amino)-thieno [2,3-d] pyridazine-7-carboxylic acid amide, 2-(3-chlorophenyl)-4-(2-tetrahydropyrrol-amino)-thieno [2,3-d] pyridazine-7-carboxylic acid amide, 2-(3-chlorophenyl)-4-(S-3-tetrahydropyrrol-amino)-thieno [2,3-d] pyridazine-7-carboxylic acid amide, 2-(3-chlorophenyl)-4-(R-3-tetrahydropyrrol-amino)-thieno [2,3-d] pyridazine-7-carboxylic acid amide, 2-(3-chlorophenyl)-4-(3-tetrahydropyrrol-amino)-thieno [2,3-d] pyridazine-7-N-methyl -carboxylic acid amide, 2-(3-fluorophenyl)-4-(3-pyridin-amino)-thieno [2,3-d] pyridazine-7-carboxylic acid amide, 2-(3-chlorophenyl)-4-(3-pyridin-amino)-thieno [2,3-d] pyridazine-7-carboxylic acid amide, 2-(3-bromophenyl)-4-(3-pyridin-amino)-thieno [2,3-d] pyridazine-7-carboxylic acid amide, 2-(3-fluorophenyl)-4-(3-α-pyran-amino)-thieno [2,3-d] pyridazine-7-carboxylic acid amide, 2-(3-chlorophenyl)-4-(3-α-pyran-amino)-thieno [2,3-d] pyridazine-7-carboxylic acid amide, 2-(3-bromophenyl)-4-(3-α-pyran-amino)-thieno [2,3-d] pyridazine-7-carboxylic acid amide, 2-(3-chlorophenyl)-4-(2-pyridin-amino)-thieno [2,3-d] pyridazine-7-carboxylic acid amide, 2-(3-chlorophenyl)-4-(4-pyridin-amino)-thieno [2,3-d] pyridazine-7-carboxylic acid amide, 2-(3-chlorophenyl)-4-(S-3-pyridin-amino)-thieno [2,3-d] pyridazine-7-carboxylic acid amide, 2-(3-chlorophenyl)-4-(R-3-pyridin-amino)-thieno [2,3-d] pyridazine-7-carboxylic acid amide, 2-(3-chlorophenyl)-4-(3-pyridin-amino)-thieno [2,3-d] pyridazine-7-N-methyl-carboxylic acid amide, 2-(3-chlorophenyl)-4-(3-pyran-amino)-thieno [2,3-d] pyridazine-7-N-methyl-carboxylic acid amide, 2-(3-fluorophenyl)-4-(3-pyrrol-amino)-thieno [2,3-d] pyridazine-7-carboxylic acid amide, 2-(3-chlorophenyl)-4-(3-pyrrol-amino)-thieno [2,3-d] pyridazine-7-carboxylic acid amide, 2-(3-bromophenyl)-4-(3-pyrrol-amino)-thieno [2,3-d] pyridazine-7-carboxylic acid amide, 2-(3-fluorophenyl)-4-(3-furan-amino)-thieno [2,3-d] pyridazine-7-carboxylic acid amide, 2-(3-chlorophenyl)-4-(3-furan-amino)-thieno [2,3-d] pyridazine-7-carboxylic acid amide, 2-(3-bromophenyl)-4-(3-furan-amino)-thieno [2,3-d] pyridazine-7-carboxylic acid amide, 2-(3-fluorophenyl)-4-(3-thieno-amino)-thieno [2,3-d] pyridazine-7-carboxylic acid amide, 2-(3-chlorophenyl)-4-(3-thieno-amino)-thieno [2,3-d] pyridazine-7-carboxylic acid amide, 2-(3-bromophenyl)-4-(3-thieno-amino)-thieno [2,3-d] pyridazine-7-carboxylic acid amide, 2-(3-chlorophenyl)-4-(2-pyrrol-amino)-thieno [2,3-d] pyridazine-7-carboxylic acid amide, 2-(3-chlorophenyl)-4-(S-3-pyrrol-amino)-thieno [2,3-d] pyridazine-7-carboxylic acid amide, 2-(3-chlorophenyl)-4-(R-3-pyrrol-amino)-thieno [2,3-d] pyridazine-7-carboxylic acid amide, 2-(3-chlorophenyl)-4-(3-pyrrol-amino)-thieno [2,3-d] pyridazine-7-N-methyl-carboxylic acid amide, 2-(3-chlorophenyl)-4-(3-thieno-amino)-thieno [2,3-d] pyridazine-7-N-methyl-carboxylic acid amide, 2-(3-chlorophenyl)-4-(3-furan-amino)-thieno [2,3-d] pyridazine-7-N-methyl-carboxylic acid amide, 2-(4-fluorophenyl)-4-(3-piperidinemethyl)-thieno [2,3-d] pyridazinyl-7-formamide, 2-(4-chlorophenyl)-4-(3-piperidinemethyl)-thieno [2,3-d] pyridazinyl-7-formamide, 2-(4-bromophenyl)-4-(3-piperidinemethyl)-thieno [2,3-d] pyridazinyl-7-formamide, 2-(4-fluorophenyl)-4-(3-tetrahydropyranmethyl)-thieno [2,3-d] pyridazinyl-7-formamide, 2-(4-chlorophenyl)-4-(3-tetrahydropyranmethyl)-thieno [2,3-d] pyridazinyl-7-formamide, 2-(4-bromophenyl)-4-(3-tetrahydropyranmethyl)-thieno [2,3-d] pyridazinyl-7-formamide, 2-(4-chlorophenyl)-4-(2-piperidinemethyl)-thieno [2,3-d] pyridazinyl-7-formamide, 2-(4-chlorophenyl)-4-(4-piperidinemethyl)-thieno [2,3-d] pyridazinyl-7-formamide, 2-(4-chlorophenyl)-4-(S-3-piperidinemethyl)-thieno [2,3-d] pyridazinyl-7-formamide, 2-(4-chlorophenyl)-4-(R-3-piperidinemethyl)-thieno [2,3-d] pyridazinyl-7-formamide, 2-(4-chlorophenyl)-4-(3-piperidinemethyl)-thieno [2,3-d] pyridazinyl-7-N-methyl -formamide, 2-(4-chlorophenyl)-4-(3-tetrahydropyranmethyl)-thieno [2,3-d] pyridazinyl-7-N-methyl-formamide, 2-(4-fluorophenyl)-4-(3-pyrrolidinemethyl)-thieno [2,3-d] pyridazinyl-7-formamide, 2-(4-chlorophenyl)-4-(3-pyrrolidinemethyl)-thieno [2,3-d] pyridazinyl-7-formamide, 2-(4-bromophenyl)-4-(3-pyrrolidinemethyl)-thieno [2,3-d] pyridazinyl-7-formamide, 2-(4-fluorophenyl)-4-(3-tetrahydrofuranmethyl)-thieno [2,3-d] pyridazinyl-7-formamide,
2-(4-chlorophenyl)-4-(3-tetrahydrofuranmethyl)-thieno [2,3-d] pyridazinyl-7-formamide,
2-(4-bromophenyl)-4-(3-tetrahydrofuranmethyl)-thieno [2,3-d] pyridazinyl-7-formamide,
2-(4-fluorophenyl)-4-(3-tetrahydrothiophenemethyl)-thieno [2,3-d] pyridazinyl-7-formamide,
2-(4-chlorophenyl)-4-(3-tetrahydrothiophenemethyl)-thieno [2,3-d] pyridazinyl-7-formamide,
2-(4-bromophenyl)-4-(3-tetrahydrothiophenemethyl)-thieno [2,3-d] pyridazinyl-7-formamide,
2-(4-chlorophenyl)-4-(S-3-pyrrolidinemethyl)-thieno [2,3-d] pyridazinyl-7-formamide,
2-(4-chlorophenyl)-4-(R-3-pyrrolidinemethyl)-thieno [2,3-d] pyridazinyl-7-formamide,
2-(4-chlorophenyl)-4-(3-pyrrolidinemethyl)-thieno [2,3-d] pyridazinyl-7-N-methyl-formamide,
2-(4-chlorophenyl)-4-(3-tetrahydrothiophenemethyl)-thieno [2,3-d] pyridazinyl-7-N-methyl-formamide,
2-(4-chlorophenyl)-4-(3-tetrahydrofuranmethyl)-thieno [2,3-d] pyridazinyl-7-N-methyl-formamide,
2-(4-fluorophenyl)-4-(3-pyridinemethyl)-thieno [2,3-d] pyridazinyl-7-formamide,
2-(4-chlorophenyl)-4-(3-pyridinemethyl)-thieno [2,3-d] pyridazinyl-7-formamide,
2-(4-bromophenyl)-4-(3-pyridinemethyl)-thieno [2,3-d] pyridazinyl-7-formamide,
2-(4-fluorophenyl)-4-(3-α-pyranmethyl)-thieno [2,3-d] pyridazinyl-7-formamide,
2-(4-chlorophenyl)-4-(3-α-pyranmethyl)-thieno [2,3-d] pyridazinyl-7-formamide,
2-(4-bromophenyl)-4-(3-α-pyranmethyl)-thieno [2,3-d] pyridazinyl-7-formamide,
2-(4-fluorophenyl)-4-(3-α-thiopyranmethyl)-thieno [2,3-d] pyridazinyl-7-formamide,
2-(4-chlorophenyl)-4-(3-α-thiopyranmethyl)-thieno [2,3-d] pyridazinyl-7-formamide,
2-(4-bromophenyl)-4-(3-α-thiopyranmethyl)-thieno [2,3-d] pyridazinyl-7-formamide,
2-(4-chlorophenyl)-4-(2-pyridinemethyl)-thieno [2,3-d] pyridazinyl-7-formamide,
2-(4-chlorophenyl)-4-(4-pyridinemethyl)-thieno [2,3-d] pyridazinyl-7-formamide,
2-(4-chlorophenyl)-4-(3-pyridinemethyl)-thieno [2,3-d] pyridazinyl-7-N-methyl formamide,
2-(4-chlorophenyl)-4-(3-thiopyranylmethyl)-thieno [2,3-d] pyridazinyl-7-N-methyl formamide,
2-(4-chlorophenyl)-4-(3-pyranmethyl)-thieno [2,3-d] pyridazinyl-7-N-methyl formamide,
2-(4-fluorophenyl)-4-(3-pyrrolemethyl)-thieno [2,3-d] pyridazinyl-7-formamide,
2-(4-chlorophenyl)-4-(3-pyrrolemethyl)-thieno [2,3-d] pyridazinyl-7-formamide,
2-(4-bromophenyl)-4-(3-pyrrolemethyl)-thieno [2,3-d] pyridazinyl-7-formamide,
2-(4-fluorophenyl)-4-(3-furanmethyl)-thieno [2,3-d] pyridazinyl-7-formamide,
2-(4-chlorophenyl)-4-(3-furanmethyl)-thieno [2,3-d] pyridazinyl-7-formamide,
2-(4-bromophenyl)-4-(3-furanmethyl)-thieno [2,3-d] pyridazinyl-7-formamide,
2-(4-fluorophenyl)-4-(3-thiaphenemethyl)-thieno [2,3-d] pyridazinyl-7-formamide,
2-(4-chlorophenyl)-4-(3-thiaphenemethyl)-thieno [2,3-d] pyridazinyl-7-formamide,
2-(4-bromophenyl)-4-(3-thiaphenemethyl)-thieno [2,3-d] pyridazinyl-7-formamide,
2-(4-chlorophenyl)-4-(2-pyrrolemethyl)-thieno [2,3-d] pyridazinyl-7-formamide,
2-(4-chlorophenyl)-4-(3-pyrrolemethyl)-thieno [2,3-d] pyridazinyl-7-N-methyl formamide,
2-(4-chlorophenyl)-4-(3-thiaphenemethyl)-thieno [2,3-d] pyridazinyl-7-N-methyl formamide, and
2-(4-chlorophenyl)-4-(3-furanmethyl)-thieno [2,3-d] pyridazinyl-7-N-methyl formamide.

16. The pharmaceutically acceptable composition according to claim 15, wherein the compound of formula I is 2-(3-fluorophenyl)-4-(3-piperidineamino)-thieno [2,3-d] pyridazine-7-carboxylic acid amide.

* * * * *